United States Patent [19]
Jacobs, Jr. et al.

[11] Patent Number: 5,981,182
[45] Date of Patent: Nov. 9, 1999

[54] VECTOR CONSTRUCTS FOR THE SELECTION AND IDENTIFICATION OF OPEN READING FRAMES

[75] Inventors: William R. Jacobs, Jr., City Island; Sabine Daugelat, Bronx, both of N.Y.

[73] Assignee: Albert Einstein College of Medicine of Yeshiva University, Bronx, N.Y.

[21] Appl. No.: 08/816,721

[22] Filed: Mar. 13, 1997

[51] Int. Cl.$^6$ .............. C12Q 1/68; C07H 21/04; C12N 15/63; C12P 21/02
[52] U.S. Cl. .......... 435/6; 435/69.1; 435/172.3; 435/320.1; 536/23.1
[58] Field of Search .............. 435/6, 320.1, 69.1, 435/172.1, 172.3; 424/130.1, 184.1, 186.1, 190.1, 191.1; 536/23.1

[56] References Cited

U.S. PATENT DOCUMENTS 5,496,714  3/1996  Comb et al. ............................ 435/65.7

OTHER PUBLICATIONS

Smith et al., "Multiplex Sequencing of 1.5 Mb of the *Mycobacterium Ieprae* Genome", Genome Research, 7: 802–819, 1997.
Norton, Microbiology, Second Ed., Addison Wesley Publishing Company, Inc., pp. 654–687, 1986.
Haynes, Science, 260: 1279–1286, 1993.
Barton F. Haynes, entitled "Scientific and Social Issues of Human Immunodeficiency Virus Vaccine Development," *Science*, vol. 260, pp. 1279–1286 May (1993).
Cynthia Friend Norton, entitled "Circulatory Infections," *Microbiology*, Chapter 22, pp. 654–687.
Douglas R. Smith, et al., entitled "Multiplex Sequencing of 1.5 Mb of the *Mycobacterium leprae* Genome," *Genome Research*, pp. 802–819, 1997.

*Primary Examiner*—Nancy Degen
*Attorney, Agent, or Firm*—Amster, Rothstein & Ebenstein

[57] ABSTRACT

The present invention provides for novel vector constructs comprising an origin of replication; a nucleotide sequence encoding an intein, the nucleotide sequence having a unique restriction enzyme site, critical amino acid residues located at the splice junctions of the intein, the intein inserted into a nucleotide sequence encoding a selectable marker; and a nucleotide sequence encoding suitable regulatory elements so as to effect expression of the vector construct in a suitable host cell. The vector constructs of the present invention may contain a DNA of interest cloned into a unique restriction site of the intein, and may be used as a vaccine alone or transformed into a vaccine vector. The vector constructs of this invention may further be used in methods of selecting translated open reading frames or genes, leading to the identification of potentially protective antigens of pathogenic organisms.

77 Claims, 17 Drawing Sheets

Tetracycline        Kanamycin

FIGURE 13
M. tuberculosis RecA Intein

```
TGCCTCGCAG AGGGCACTCG GATCTTCGAT CCGGTCACCG GTACAACGCA    50
TCGCATCGAG GATGTTGTCG ATGGGCGCAA GCCTATTCAT GTCGTGGCTG   150
CTGCCAAGGA CGGAACGCTG CATGCGCGGC CCGTGGTGTC CTGGTTCGAC   200
CAGGGAACGC GGGATGTGAT CGGGTTGCGG ATCGCCGGTG GCGCCATCGT   250
GTGGGCGACA CCCGATCACA AGGTGCTGAC AGAGTACGGC TGGCGTGCCG   300
CCGGGGAACT CCGCAAGGGA GACAGGGTGG CGCAACCGCG ACGCTTCGAT   350
GGATTCGGTG ACAGTGCGCC GATTCCGGCG GATCATGCCC GGCTGCTTGG   400
CTACCTGATC GGAGATGGCA GGGATGGTTG GGTGGGGGGC AAGACTCCGA   450
TCAACTTCAT CAATGTTCAG CGGGCGCTCA TTGACGACGT GACGCGAATC   500
GCTGCGACGC TCGGTTGCGC GGCCCATCCG CAGGGGCGTA TCTCACTCGC   550
GATCGCTCAT CGACCCGGTG AGCGCAACGG TGTGGCAGAC CTTTGTCAGC   600
AGGCCGGTAT CTACGGCAAG CTCGCGTGGG AGAAGACGAT TCCGAATTGG   650
TTCTTCGAGC CGGACATCGC GGCCGACATT GTCGGCAATC TGCTCTTCGG   700
CCTGTTCGAA AGCGACGGGT GGGTGAGCCG GAACAGACC GGGGCACTTC   750
GGGTCGGTTA CACGACGACC TCTGAACAAC TCGCGCATCA GATTCATTGG   800
CTGCTGCTGC GGTTCGGTGT CGGGAGCACC GTTCGAGATT ACGATCCGAC   850
CCAGAAGCGG CCGAGCATCG TCAACGGTCG ACGGATCCAG AGCAAACGTC   900
AAGTGTTCGA GGTCCGGATC TCGGGTATGG ATAACGTCAC GGCATTCGCG   950
GAGTCAGTTC CCATGTGGGG GCCGCGCGGT GCCGCGCTTA TCCAGGCGAT  1000
TCCAGAAGCC ACGCAGGGGC GGCGTCGTGG ATCGCAAGCG ACATATCTGG  1050
CTGCAGAGAT GACCGATGCC GTGCTGAATT ATCTGGACGA GCGCGGCGTG  1100
ACCGCGCAGG AGGCCGCGGC CATGATCGGT GTAGCTTCCG GGACCCCCG   1150
CGGTGGAATG AAGCAGGTCT TAGGTGCCAG CCGCCTTCGT CGGGATCGCG  1200
TGCAGGCGCT CGCGGATGCC CTGGATGACA AATTCCTGCA CGACATGCTG  1250
GCGGAAGAAC TCCGCTATTC CGTGATCCGA GAAGTGCTGC CAACGCGGCG  1300
GGCACGAACG TTCGACCTCG AGGTCGAGGA ACTGCACACC CTCGTCGCCG  1350
AAGGGGTTGT CGTGCACAAC TGT                              1373
```

FIGURE 14 pYUB763 Nucleic Acid Sequence

```
AATTCTCATG TTTGACAGCT TATCATCGCG ATAAGCTTTA ATGCGGTAGT      50
TTATCACAGT TAAATTGCTA ACGCAGTCAG GCACCGTGTA TGAAATCTAA     100
CAATGCGCTC ATCGTCATCC TCGGCACCGT CACCCTGGAT GCTGTAGGCA     150
TAGGCTTGGT TATGCCGGTA CTGCCGGGCC TCTTGCGGGA TATCGTCCAT     200
TCCGACAGCA TCGCCAGTCA CTATGGCGTG CTGCTAGCGC TATATGCGTT     250
GATGCAATTT CTATGCGCAC CCGTTCTCGG AGCACTGTCC GACCGCTTTG     300
GCCGCCGCCC AGTCCTGCTC GCTTCGCTAC TTGGAGCCAC TATCGACTAC     350
GCGATCATGG CGACCACACC CGTCCTGTGG ATCCTCTACG CCGGACGCAT     400
CGTGGCCGGC ATCACCGGCG CCACAGGTGC GGTTGCTGGC GCCTATATCG     450
CCGACATCAC CGATGGGGAA GATCGGGCTC GCCACTTCGG GCTCATGAGC     500
GCTTGTTTCG GCGTGGGTAT GGTGGCAGGC CCCGTGGCCG GGGACTGTT      550
GGGCGCCATC TCCTTGCATG CACCATTCCT TGCGGCGGCG GTGCTCAACG     600
GCCTCAACCT ACTACTGGGC TGCTTCCTAA TGCAGGAGTC GCATAAGGGA     650
GAGCGTCGAC CGATGCCCTT GAGAGCCTTC AACCCAGTCA GCTCCTTCCG     700
GTGGGCGCGG GGCATGACTA TCGTCGCCGC ACTTATGACT GTCTTCTTTA     750
TCATGCAACT CGTAGGACAG GTGCCGGCAG CGCTCTGGGT CATTTTCGGC     800
GAGGACCGCT TTCGCTGGAG CGCGACGATG ATCGGCCTGT CGCTTGCGGT     850
ATTCGGAATC TTGCACGCCC TCGCTCAAGC CTTCGTCACT GGTCCCGCCA     900
CCAAACGTTT CGGCGAGAAG CAGGCCATTA TCGCCGGCAT GGCGGCCGAC     950
GCGCTGGGCT ACGTCTTGCT GGCGTTCGCG ACGCGAGGCT GGATGGCCTT    1000
CCCCATTATG ATTCTTCTCG CTTCCGGCGG CATCGGGATG CCCGCGTTGC    1050
AGGCCATGCT GTCCAGGCAG GTAGATGACG ACCATCAGGG ACAGCTTCAA    1100
GGATCGCTCG CGGCTCTTAC CAGCCTAACT TCGATCACTG GACCGCTGAT    1150
CGTCACGGCG ATTTATGCCG CCTCGGCGAG CACATGGAAC GGGTTGGCAT    1200
GGATTGTAGG CGCCGCCCTA TACCTTGTCT GCCTCCCCGC GTTGCGTCGC    1250
GGTGCATGGA GCCGGGCCAC CTCGACCTGA ATGGAAGCCG GCGGCACCTC    1300
GCTAACGGAT TCACCACTCC AAGAATTGGA GCCAATCAAT TCTTGCGGAG    1350
AACTGTGAAT GCGCAAACCA ACCCTTGGCA GAACATATCC ATCGCGTCCG    1400
CCATCTCCAG CAGCCGCACG CGGCGCATCT CGGGCAGCGT TGGGTCCTGG    1450
CCACGGGTGC GCATGATCGT GCTCCTGTCG TTGAGGACCC GGCTAGGCTG    1500
GCGGGGTTGC CTTACTGGTT AGCAGAATGA ATCACCGATA CGCGAGCGAA    1550
CGTGAAGCGA CTGCTGCTGC AAAACGTCTG CGACCTGAGC AACAACATGA    1600
```

FIGURE 14, CONT.

```
ATGGTCTTCG GTTTCCGTGT TTCGTAAAGT CTGGAAACGC GGAAGTCAGC      1650
GCCCTGCACC ATTATGTTCC GGATCTGCAT CGCAGGATGC TGCTGGCTAC      1700
CCTGTGGAAC ACCTACATCT GTATTAACGA AGCGCTGGCA TTGACCCTGA      1750
GTGATTTTTC TCTGGTCCCG CCGCATCCAT ACCGCCAGTT GTTTACCCTC      1800
ACAACGTTCC AGTAACCGGG CATGTTCATC ATCAGTAACC CGTATCGTGA      1850
GCATCCTCTC TCGTTTCATC GGTATCATTA CCCCATGAA CAGAAATTCC       1900
CCCTTACACG GAGGCATCAA GTGACCAAAC AGGAAAAAAC CGCCCTTAAC      1950
ATGGCCCGCT TTATCAGAAG CCAGACATTA ACGCTTCTGG AGAAACTCAA      2000
CGAGCTGGAC GCGGATGAAC AGGCAGACAT CTGTGAATCG CTTCACGACC      2050
ACGCTGATGA GCTTTACCGC AGAACGAGGA CAGTCGCACG ACGAAGTTCT      2100
TCTGGATCGC GCCCGTGCTG GAAGCACTCA ACCTCGAAGC GTGTGGTTGC      2150
GGAGCCATCT AGCAACCACA CGAAACATGC GCAACGAACC GCGCAACGAA      2200
CAACGCCTAG AACTGGCACT AGATGAGCTG ACTCGTATCG TTGGTAAACC      2250
TAGTTTGACC AGCATGTTTT AACTACGTTC GGTGAGCTGT CAACGGGGCC      2300
TGTAACGGCA CAACGAACCG TGCAACGAGA GTGGCCACGG ATGCCACCAC      2350
AAGCACTACA ACGGAGTTCG CCACGTAGCG ATAGCGGAGT GTATACTGGC      2400
TTAACTATGC GGCATCAGAG CAGATTGTAC TGAGAGTGCA CCATATGCGG      2450
TGTGAAATAC CGCACAGATG CGTAAGGAGA AAATACCGCA TCAGGCGCTC      2500
TTCCGCTTCC TCGCTCACTG ACTCGCTGCG CTCGGTCGTT CGGCTGCGGC      2550
GAGCGGTATC AGCTCACTCA AAGGCGGTAA TACGGTTATC CACAGAATCA      2600
GGGGATAACG CAGGAAAGAA CATGTGAGCA AAAGGCCAGC AAAAGGCCAG      2650
GAACCGTAAA AAGGCCGCGT TGCTGGCGTT TTTCCATAGG CTCCGCCCCC      2700
CTGACGAGCA TCACAAAAAT CGACGCTCAA GTCAGAGGTG GCGAAACCCG      2750
ACAGGACTAT AAAGATACCA GGCGTTTCCC CCTGGAAGCT CCCTCGTGCG      2800
CTCTCCTGTT CCGACCCTGC CGCTTACCGG ATACCTGTCC GCCTTTCTCC      2850
CTTCGGGAAG CGTGGCGCTT TCTCAATGCT CACGCTGTAG GTATCTCAGT      2900
TCGGTGTAGG TCGTTCGCTC CAAGCTGGGC TGTGTGCACG AACCCCCCGT      2950
TCAGCCCGAC CGCTGCGCCT TATCCGGTAA CTATCGTCTT GAGTCCAACC      3000
CGGTAAGACA CGACTTATCG CCACTGGCAG CAGCCACTGG TAACAGGATT      3050
AGCAGAGCGA GGTATGTAGG CGGTGCTACA GAGTTCTTGA AGTGGTGGCC      3100
TAACTACGGC TACACTAGAA GGACAGTATT TGGTATCTGC GCTCTGCTGA      3150
AGCCAGTTAC CTTCGGAAAA AGAGTTGGTA GCTCTTGATC CGGCAAACAA      3200
ACCACCGCTG GTAGCGGTGG TTTTTTTGTT TGCAAGCAGC AGATTACGCG      3250
CAGAAAAAAA GGATCTCAAG AAGATCCTTT GATCTTTTCT ACGGGGTCTG      3300
```

FIGURE 14, CONT.

```
ACGCTCAGTG GAACGAAAAC TCACGTTAAG GGATTTTGGT CATGAGATTA      3350
TCAAAAAGGA TCTTCACCTA GATCCTTTTA TTATTGAAGC ATTTATCAGG      3400
GTTATTGTCT CATGAGCGGA TACATATTTG AATGTATTTA GAAAAATAAA      3450
CAAATAGGGG TTCCGCGCAC ATTTCCCCGA AAAGTGCCAC CTGACGTCTA      3500
AGAAACCATT ATTATCATGA CATTAACCTA TAAAAATAGG CGTATCACGA      3550
GGCCCTTTCG TCTTCAAGAA TTCCCGGATC CGTCGACCTG CAGGGGGGGC      3600
GCTGAGGTCT GCCTCGTGAA GAAGGTGTTG CTGACTCATA CCAGGCCTGA      3650
ATCGCCCCAT CATCCAGCCA GAAAGTGAGG GAGCCACGGT TGATGAGAGC      3700
TTTGTTGTAG GTGGACCAGT TGGTGATTTT GAACTTTTGC TTTGCCACGG      3750
AACGGTCTGC GTTGTCGGGA AGATGCGTGA TCTGATCCTT CAACTCAGCA      3800
AAAGTTCGAT TTATTCAACA AAGCCGCCGT CCCGTCAAGT CAGCGTAATG      3850
CTCTGCCAGT GTTACAACCA ATTAACCAAT TCTGATTAGA AAAACTCATC      3900
GAGCATCAAA TGAAACTGCA ATTTATTCAT ATCAGGATTA TCAATACCAT      3950
ATTTTTGAAA AAGCCGTTTC TGTAATGAAG GAGAAAACTC ACCGAGGCAG      4000
TTCCATAGGA TGGCAAGATC CTGGTATCGG TCTGCGATTC CGACTCGTCC      4050
AACATCAATA CAACCTATTA ATTTCCCTCG TCAAAAATA AGGTTATCAA       4100
GTGAGAAATC ACCATGAGTG ACGACTGAAT CCGGTGAGAA TGGCAAAAGC      4150
TTATGCATTT CTTTCCAGAC TTGTTCAACA GGCCAGCCAT TACGCTCGTC      4200
ATCAAAATCA CTCGCATCAA CCAAACCGTT ATTCATTCGT GATTGCGCCT      4250
GAGCGAGACG AAATACGCGA TCGCTGTTAA AAGGACAATT ACAAACAGGA      4300
ATCGAATGCA ACCGGCGCAG GAACACTGCC AGCGCATCAA CAATACAGTT      4350
GTGCACGACA ACCCCTTCGG CGACGAGGGT GTGCAGTTCC TCGACCTCGA      4400
GGTCGAACGT TCGTGCCCGC CGCGTTGGCA GCACTTCTCG GATCACGGAA      4450
TAGCGGAGTT CTTCCGCCAG CATGTCGTGC AGGAATTTGT CATCCAGGGC      4500
ATCCGCGAGC GCCTGCACGC GATCCCGACG AAGGCGGCTG GCACCTAAGA      4550
CCTGCTTCAT TCCACCGCGG GGGTCCCCGG AAGCTACACC GATCATGGCC      4600
GCGGCCTCCT GCGCGGTCAC GCCGCGCTCG TCCAGATAAT TCAGCACGGC      4650
ATCGGTCATC TCTGCAGCCA GATATGTCGC TTGCGATCCA CGACGCCGCC      4700
CCTGCGTGGC TTCTGGAATC GCCTGGATAA GCGCGGCACC GCGCGGCCCC      4750
CACATGGGAA CTGACTCCGC GAATGCCGTG ACGTTATCCA TACCCGAGAT      4800
CCGGACCTCG AACACTTGAC GTTTGCTCTG GATCCGTCGA CCGTTGACGA      4850
TGCTCGGCCG CTTCTGGGTC GGATCGTAAT CTCGAACGGT GCTCCCGACA      4900
CCGAACCGCA GCAGCAGCCA ATGAATCTGA TGCGCGAGTT GTTCAGAGGT      4950
CGTCGTGTAA CCGACCCGAA GTGCCCCGGT CTGTTCCCGG CTCACCCACC      5000
```

FIGURE 14, CONT.

| | | | | | |
|---|---|---|---|---|---|
| CGTCGCTTTC | GAACAGGCCG | AAGAGCAGAT | TGCCGACAAT | GTCGGCCGCG | 5050 |
| ATGTCCGGCT | CGAAGAACCA | ATTCGGAATC | GTCTTCTCCC | ACGCGAGCTT | 5100 |
| GCCGTAGATA | CCGGCCTGCT | GACAAAGGTC | TGCCACACCG | TTGCGCTCAC | 5150 |
| CGGGTCGATG | AGCGATCGCG | AGTGAGATAC | GCCCCTGCGG | ATGGGCCGCG | 5200 |
| CAACCGAGCG | TCGCAGCGAT | TCGCGTCACG | TCGTCAATGA | GCGCCCGCTG | 5250 |
| AACATTGATG | AAGTTGATCG | GAGTCTTGCC | CCCCACCCAA | CCATCCCTGC | 5300 |
| CATCTCCGAT | CAGGTAGCCA | AGCAGCCGGG | CATGATCCGC | CGGAATCGGC | 5350 |
| GCACTGTCAC | CGAATCCATC | GAAGCGTCGC | GGTTGCGCCA | CCCTGTCTCC | 5400 |
| CTTGCGGAGT | TCCCCGGCGG | CACGCCAGCC | GTACTCTGTC | AGCACCTTGT | 5450 |
| GATCGGGTGT | CGCCCACACG | ATGGCGCCAC | CGGCGATCCG | CAACCCGATC | 5500 |
| ACATCCCGCG | TTCCTGGTC | GAACCAGGAC | ACCACGGGCC | GCGCATGCAG | 5550 |
| CGTTCCGTCC | TTGGCAGCAG | CCACGACATG | AATAGGCTTG | CGCCCATCGA | 5600 |
| CAACATCCTC | GATGCGATGC | GTTGTACCGG | TGACCGGATC | GAAGATCCGA | 5650 |
| GTGCCCTCTG | CGAGGCAATT | TTCACCTGAA | TCAGGATATT | CTTCTAATAC | 5700 |
| CTGGAATGCT | GTTTTCCCGG | GGATCGCAGT | GGTGAGTAAC | CATGCATCAT | 5750 |
| CAGGAGTACG | GATAAAATGC | TTGATGGTCG | GAAGAGGCAT | AAATTCCGTC | 5800 |
| AGCCAGTTTA | GTCTGACCAT | CTCATCTGTA | ACATCATTGG | CAACGCTACC | 5850 |
| TTTGCCATGT | TTCAGAAACA | ACTCTGGCGC | ATGGGCTTC | CCATACAATC | 5900 |
| GATAGATTGT | CGCACCTGAT | TGCCCGACAT | TATCGCGAGC | CCATTTATAC | 5950 |
| CCATATAAAT | CAGCATCCAT | GTTGGAATTT | AATCGCGGCC | TCGAGCAAGA | 6000 |
| CGTTTCCCGT | TGAATATGGC | TCATAACACC | CCTTGTATTA | CTGTTTATGT | 6050 |
| AAGCAGACAG | TTTTATTGTT | CATGATGATA | TATTTTTATC | TTGTGCAATG | 6100 |
| TAACATCAGA | GATTTTGAGA | CACAACGTCG | CTTTGTTGAA | TAAATCGAAC | 6150 |
| TTTTGCTGAG | TTGAAGGATC | AGATCACGCA | TCTTCCCGAC | AACGCAGACC | 6200 |
| GTTCCGTGGC | AAAGCAAAAG | TTCAAAATCA | CCAACTGGTC | CACCTACAAC | 6250 |
| AAAGCTCTCA | TCAACCGTGG | CTCCCTCACT | TTCTGGCTGG | ATGATGGGGC | 6300 |
| GATTCAGGCC | TGGTATGAGT | CAGCAACACC | TTCTTCACGA | GGCAGACCTC | 6350 |
| AGCGCCCCCC | TGCAGGTCGA | CGGATCCGGG | G | | 6381 |

VECTOR CONSTRUCTS FOR THE SELECTION AND IDENTIFICATION OF OPEN READING FRAMES

BACKGROUND OF THE INVENTION

Knowledge about protective antigens of a pathogen is currently considered a prerequisite for vaccine development. Selection of relevant antigens is accomplished by standard immunological techniques, such as immunization of animals, in vitro T- and B-cell stimulation assays, as well as biochemical studies. Several important vaccines have been constructed as a result of such investigations. However, a number of significant infectious diseases, such as tuberculosis, malaria, and HIV, are still awaiting development of effective vaccines.

Employing genomic libraries of a pathogen (to encode for a large collection of antigens) rather than analyzing in vitro expressed proteins, would ensure that the complete antigenic information of an organism is represented and would also overcome the problem that in vitro produced proteins can differ significantly from those synthesized in vivo. The use of genomic libraries to search for protective antigens, however, is hindered by the large number of constructs which have to be screened because there is no selection system which identifies well expressed open reading frames while discriminating against those fragments that contain non-coding DNA sequences or stop codons. DNA vaccination techniques allow to immunize animals directly with constructs containing genetic material of a pathogen, and to measure its protective value by challenging with the infectious agent. Using this approach, single antigens of *Mycobacteria tuberculosis* (the heat shock protein hsp65, the 36 kDa proline-rich antigen and the antigen 85 complex) have recently been tested, and shown to confer comparable levels of protection as *Mycobacterium bovis*-BCG (Tascon, et al., *Nature Medicine*, 2:888–892 (1996); Huygen, et al. *Nature Medicine*, 2:893–898 (1996)). Additionally, complete genomic expression libraries of *Mycoplasma pulmonis* have been constructed, and nucleic acid immunization employing such libraries proved to be protective in mice (Barry, et al., *Nature*, 377:632–635 (1995)). However, as powerful as this new strategy is, it is difficult to recover constructs from surviving animals and identify individual protective antigens.

Therefore, there remains a need for an improved method of identification of potential protective antigens of pathogenic organisms for which effective vaccines are not yet available. Current methods employ genomic libraries to search for protective antigens. A problem with libraries of randomly cloned genetic material is that they contain very little coding sequences. Accordingly, as there is currently no selection system for well expressed open reading frames, a great number of clones might have to be analyzed in order to find whole or partial open reading frames. Therefore, methods are needed for the selection and identification of whole and partial open reading frames from a genomic library in order to ultimately identify protective antigens.

The concept of the present invention is based upon the unique protein splicing properties of a novel class of genetic elements once referred to as "intervening protein sequences", now correctly called "inteins" (Perler, et al., *Nucleic Acids Research*, 22:1125–1127 (1994)). Inteins were first discovered in 1990 when one was found in a yeast gene (Kane, et al., *Science*, 250:651–657 (1990)); Hirata, et al., *J. Biol. Chem.*, 265:6726–6733 (1990)). The investigators aligned the vacuolar ATPase VMA1 gene of *Saccharomyces cerevisiae* to similar genes from other organisms, and observed strong homology at both ends of the gene, but also found a large portion in the middle of the gene had very little homology to other ATPases. Furthermore, the *S. cerevisiae* VMA1 gene was much larger than any other known similar gene, while the gene produce was of the same size as other ATPases. After careful analysis of the transcription and translation process, the possibility of RNA splicing was ruled out, and the investigators concluded that protein splicing was occurring (Kane, et al., *Science*, 250:651–657 (1990)); Hirata, et al., *J. Biol. Chem.*, 265:6726–6733 (1990)). Since then, more cases of protein splicing have been found, and currently about 10 to 15 inteins have been identified (reviewed in Clyman, *ASM News*, 61:344–347 (1995); Colston and Davis, *Mol. Microbiol.*, 12:359–363 (1994)). Inteins could be demonstrated in eukaryotes, eubacteria and archae, thus spanning all three kingdoms. Very recently, the complete genome sequence of an archaeon, *Methanococcus jannaschii*, was published, and in the 38% of its genome which has homology to known genes from other organism, 18 inteins were identified, of which only 2 had been previously recognized (Bult, et al., *Science*, 273:1058–1073 (1996)). Inteins have very little homology to each other, making it hard to identify new members of this class of genetic elements in databases (Pietrokowsky, 1994). Basically every intein described so far has been discovered accidentally when the researchers tried to clone a gene and aligned it with already known sequences. Inteins can be defined as protein sequences which are embedded in frame within a precursor protein, and which are removed by protein splicing. During that process, the two terminal portions become ligated by a peptide bond, and form a fusion protein which is called the host protein or extein. The amino acids found at the two hexapeptide motifs on each end of the intein are crucial for the splicing process. These regions, which are also called splice sites, are extremely conserved in all inteins. The mechanism of protein splicing is not entirely understood, but involves several of these amino acids, particularly the C-terminal histidine, asparagine and cysteine/threonine/serine residues (Davis, et al., *J. Bacteriol.*, 173:5653–5662 (1992); Hirata and Anraku, *Biochem. Biophy. Res. Comm.*, 188:40–47 (1992); Hodges, et al., *Nucleic Acids Research*, 20:6153–6157 (1992); Cooper, et al., *EMBO Journal*, 12:2575–2583 (1993)). Splicing appears to be autocatalytical, and does not require any host cell cofactor, since inteins can splice out of their precursor proteins in a variety of in vivo and in vitro expression systems, including phosphate buffered saline (Davis, et al., *J. Bacteriol.*, 173:5653–5662 (1992); Xu, et al., *Cell*, 75:1371–1377 (1993); and reviewed in Colston and Davis, *Mol. Micobiol.*, 12:359–363 (1994)). Hallmarks of protein splicing are that most of the amino acids of the splice sites cannot be altered at the translation level, and that most deletions, stop codons, as well as any frame shifts within the intein are deleterious. Most inteins described so far possess a second characteristic pattern, as they show homology to the HO endonuclease motifs found in group 1 RNA introns, which is seen in the central part of the intein (reviewed in Belfort, et al., *J. Bacteriol.*, 177:3897–3903 (1995)). In fact, it has been reported that several inteins display restriction endonuclease activity once they have spliced out of their host proteins (Shub and Goodrich-Blair, *Cell*, 71:183–186 (1992)). An actual homing function which is characteristic for group 1 RNA intron endonucleases has so far only been demonstrated for VMA1 intein of *S. cerevisiae* (Gimble and Thorner, *Nature*, 357:301–306 (1992); Gimble and Thorner, *J. Biol. Chem.*, 268:21844–21853 (1993)).

SUMMARY OF THE INVENTION

The present invention provides for novel vector constructs. Specifically, the novel vector constructs of the present invention comprise an origin of replication, a selectable marker gene, a nucleotide sequence encoding an intein, said nucleotide sequence having a unique restriction enzyme site, a nucleotide sequence encoding critical amino acid residues located at the splice junctions of said intein, and a nucleotide sequence encoding suitable regulatory elements so as to effect expression of the vector construct in a suitable host cell.

The present invention further provides for the vector constructs of the present invention further containing a DNA of interest cloned into a unique restriction site of the DNA sequence encoding an intein. The present invention additionally provides the use of the vector constructs containing a DNA of interest as a vaccine.

The present invention also provides for vector constructs of the present invention that contain the DNA of interest transformed into a vaccine vector, and the use of these constructs as a vaccine. Further, the present invention provides for use of the vector constructs of the present invention for the identification of a DNA sequence as an open reading frame sequence. Specifically, the vector constructs of the present invention may be used in methods of selecting translated open reading frames or genes, leading to the identification of potentially protective antigens of pathogenic organisms.

Additional objects of the invention will be apparent from the description which follows.

BRIEF DESCRIPTION OF THE FIGURES

FIG. 1 sets forth maps of the plasmids pYUB53, pYUB750, pYUB751, pYUB752, and pYUB758. The maps show plasmid size, location of antibiotic resistance, markers, sites for restriction endonucleases, and the insertion points and orientation of the *M. tuberculosis* recA intervening sequence.

FIG. 2 sets forth the results of an analysis of the orientation of inserts in various plasmid DNAs digested with PinAI. The plasmids analyzed were pYUB53, pYUB750, pYUB751, pYUB752, pYUB753, pYUB754, pYUB755, pYUB756, pYUB757, and pYUB758. Approximately 150 ng of DNA was loaded on each lane of a 0.7% agarose gel, separated by electrophoresis and stained with ethidium bromide. A lambda Bst EII digest was used as a DNA standard.

FIG. 3 sets forth the results of a minicell analysis of gene products in plasmid constructs.

FIG. 4 sets forth a graphic representation of the position of the BglII site in mutated plasmids pYUB759, pYUB763, and pYUB764.

FIG. 5 sets forth the results of diagnostic double digests of plasmids carrying a BglII insert. DNA from plasmids pYUB758, pYUB759, pYUB763, and pYUB764 was digested with BglII and EcoRV. The far left column shows a lambda Bst EII digest which was used as a DNA standard.

FIG. 6 sets forth the results of a minicell analysis of gene products in plasmids with a BglII insertion. The plasmids analyzed were pYUB758, pYUB759, pYUB763, pYUB764 (clone #2), pYUB764 (clone #4), pYUB764 (clone #13), pYUB764 (clone #14), and pYUB764 (clone #15).

FIG. 7 sets forth a graphic representation of the insertion of the influenza hemagglutinin (HA) epitope into the BglII site of plasmid pYUB763. The restriction sites for BglII and BamHI, which were added to the sequence of the HA epitope, are depicted in lower case.

FIG. 8 sets forth the results of diagnostic double digests of HA tagged plasmids with BglII and AspI. DNA from the indicated plasmids was digested with BglII and AspI. A 100 base pair ladder was used as a control.

FIGS. 9A and 9B set forth the results of a minicell analysis of gene products in HA tagged plasmids. [$^{14}$C]-labeled rainbow markers (Amersham) were used as protein standards. FIG. 9A sets forth the results after ECL detection and exposure to an X-ray film for 3 days. FIG. 9B sets forth HA peptide detection with mouse monoclonal antibody 12CA5 (Boehringer Mannheim) and visualized with the ECL system.

FIG. 10 sets forth results of a minicell analysis of gene products in plasmids with inserted mycobacteriophage L5 DNA fragments. DNA from indicated plasmids was transformed into *E. coli* P678-54. Minicells were separated, and newly synthesized proteins were labelled with [$^{35}$S]-methionine. Proteins were separated on a 10% polyacrylamide gel, loading 50,000 cpm per lane. [$^{14}$C]-labeled rainbow markers (Amersham) were used as protein standards. The gel was fixed, treated with Amplify, dried, and exposed for 2 days to an X-ray film.

FIG. 11 sets forth the results of double restriction digests of plasmids carrying Bgl II linker mutations in the *M. tuberculosis* recA intein. DNA from indicated plasmids was digested with Bgl II and EcoRV. Approximately 250 ng of DNA was loaded on each lane of a 0.7% agarose gel, separated by electrophoresis and stained with ethidium bromide. A lambda Bst EII digest was used as a DNA standard; DNA marker fragments are shown in lanes 1 and 14 (size indicated in kbp).

FIG. 12 sets forth the results of the growth of *E. coli* transformed with plasmids carrying BglII linker mutations in the *M. tuberculosis* recA intein. *E. coli* were transformed with indicated plasmids, and grown in LB medium containing tetracycline (12.5 μg per ml) until stationary. Of these cultures, 50 μl were spotted onto LB plates containing either tetracycline (12.5 μg per ml) or kanamycin (35 μg per ml). Spots were allowed to dry, and plates were incubated for one day at 37° C., and one day at 30° C.

FIG. 13: FIG. 13 sets forth the nucleotide sequence of the *M. tuberculosis* recA intein.

FIG. 14: FIG. 14 sets forth the nucleotide sequence of the plasmid pYUB763.

DETAILED DESCRIPTION OF THE INVENTION

Figure 1:
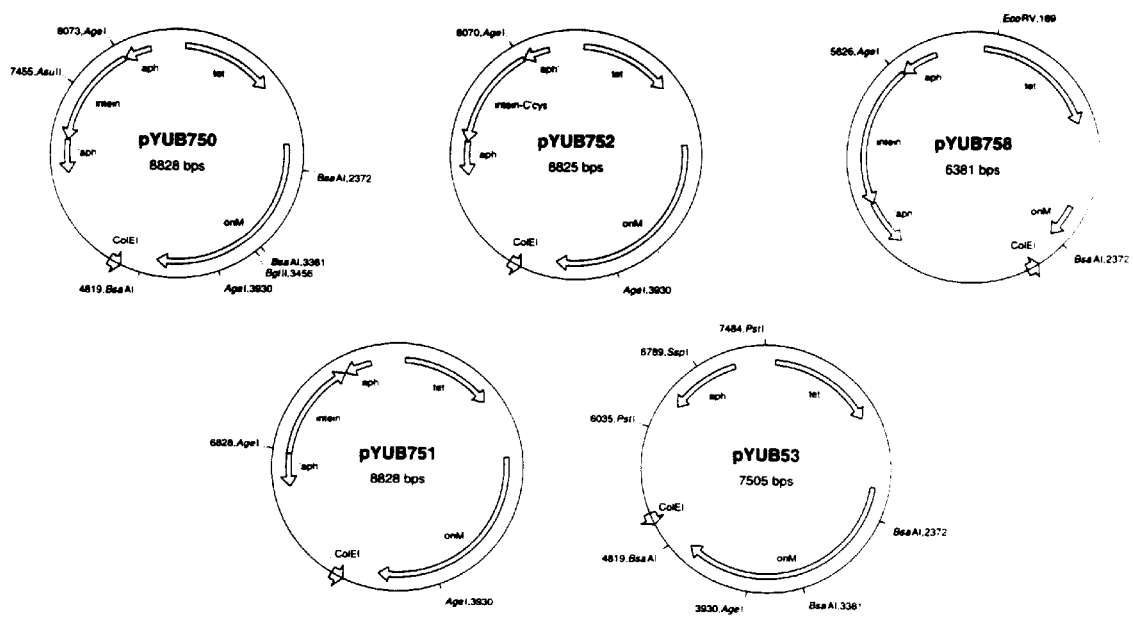
FIG. 1.

The present invention provides for novel vector constructs for use in methods of the selection and identification of a DNA of interest. The vector constructs of the present invention may be used to select open reading frame DNA sequences from genomic libraries, leading to the identification of potentially protective antigens of pathogenic organisms.

Specifically, the novel vector constructs of the present invention comprise an origin of replication, a selectable marker gene, a nucleotide sequence encoding an intein, said nucleotide sequence having a unique restriction enzyme site, a nucleotide sequence encoding critical amino acid residues located at the splice junctions of said intein, and a nucleotide sequence encoding suitable regulatory elements so as to effect expression of the vector construct in a suitable host cell.

The vector constructs of the present invention contain origins of replication necessary for amplification in a specific host cell. In a preferred embodiment of the invention, the oriM mycobacterial origin of replication is reconstituted for amplification in a mycobacterial host cell. Further non-limiting examples of bacterial origins of replication that may be used in the vector constructs of the present invention are an *E. coli* origin of replication, a Salmonella origin of replication, a Shigella origin of replication, a Bacillus origin of replication, a Staphylococcus origin of replication, or a pneumococcal origin of replication. The vector constructs of the present invention can be designed to contain the appropriate regulatory sequences and all of the necessary DNA elements for integration of the construct, and/or the appropriate components thereof, and expression of a gene of interest in a given cell type.

The vector constructs of the present invention contain a DNA sequence encoding an intein. An intein is herein defined as a protein sequence which, during protein splicing, is excised from a protein precursor. The DNA sequences encoding the inteins may be obtained from a prokaryotic DNA sequence, such as a bacterial DNA sequence, or a eukaryotic DNA sequence, such as a yeast DNA sequence. Examples of bacteria from which the DNA sequences encoding the inteins of the present invention may be obtained include, but are not limited to, *Mycobacterium bovis* BCG, *Mycobacterium leprae, Mycobacterium flavescens, Mycobacterium gordoneae, Mycobacterium xenopi, Mycobacterium kansasii, Mycobacterium microti, Mycobacterium tuberculosis*, and the archaebacteria *Pyrococcus species, Thermococcus litoralis*, and *Methanococcus jannaschii*. Examples of yeast from which the inteins of the present invention may be obtained include, but are not limited to, *Saccharomyces cerevisiae* and *Candida tropicalis*. Specific non-limiting examples of DNA sequences encoding inteins for use in the vector constructs of the present invention include *Thermococcus litoralis* DNA polymerase (Tli pol intein-1 and Tli pol intein-2), Psp IVPS1, *Mycobacterial tuberculosis* RecA, Pyrococcus polymerase intein (Psp pol intein), and the *Saccharomyces cerevisiae* TFP1 (Sce VMA intein). In a preferred embodiment of the invention, the vector constructs employ the DNA sequence encoding the recA intein which is found in the DNA repair enzyme recA of mycobacteria. The nucleotide sequence of the recA intein of *M. tuberculosis* is set forth in FIG. 13. The DNA sequence encoding an intein can be obtained from natural sources or by synthetic means. For example, the DNA sequence encoding an intein may be obtained through PCR amplification of the intein using genomic DNA of a particular organism. Alternatively, the DNA sequences encoding an intein can be synthesized by conventional techniques of DNA synthesis.

The DNA sequences encoding inteins found in the vector constructs of the present invention contain DNA sequences encoding critical amino acid residues located at the splice junctions of the intein. The splice junctions are situated at the N'- and C'- terminal ends of the intein. The critical amino acid residues located at the splice junctions of the inteins are those residues which are necessary for the splicing of the intein from the precursor protein. These amino acids may be, among others, histidine, asparagine, cysteine, threonine, or serine residues. In a preferred embodiment of the invention, in order to ensure that the intein would be spliced from the precursor protein, the DNA sequence encoding the last C'-terminal cysteine codon, provided by the recA host gene, was amplified together with the DNA sequence encoding the intein. This step was necessary because the cysteine residue is required for protein splicing, but the DNA sequence encoding the cysteine residue would not be provided by the aph gene at the intended insertion point. Alternatively, the DNA sequence encoding the amino acid residues necessary for splicing of the particular intein may be synthetically added, or they may be provided by the sequence of the selectable marker.

The vector constructs of the present invention also contain a unique restriction site positioned within the intein, which is necessary for cloning into the DNA sequence of the intein a DNA of interest. The restriction site may be inserted into the DNA sequence encoding the intein, or it may be an existing restriction site within the intein.

As used herein, a "DNA of interest" is any translated open reading frame. A translated open reading frame is a DNA sequence that is transcribed continuously into mRNA, and then translated continuously into an amino acid sequence, uninterrupted by stop codons. The translated open reading frame may be all or a portion of a gene encoding a protein or polypeptide. A non-limiting example of a DNA of interest includes those sequences that encode antigens. Antigens for which the DNA of interest may encode include, but are not limited to, *Mycobacterium leprae* antigens, *Mycobacterium tuberculosis* antigens, *Mycoplasma pulmonis* antigens, *Mycobacterium bovis* BCG antigens, Mycobacteriophage L5, Rickettsia antigens, malaria sporozoites and merozoites, diptheria toxoids, tetanus toxoids, Clostridium antigens, Leishmania antigens, Salmonella antigens, Borrelia antigens, *Mycobacterium africanum* antigens, *Mycobacterium avium* antigens, *Mycobacterium intracellulare* antigens, Treponema antigens, Pertussis antigens, Schistose antigens, Filaria antigens, Herpes virus antigens, Shigella antigens, Neiserria antigens, *Haemophilus influenzae* antigens, pseudorabies virus antigens, rabies antigens, polio virus antigens, Rift Valley Fever virus antigens, dengue virus antigens, human immunodeficiency virus antigens, respiratory syncytial virus antigens, snake venom antigens, and *Vibrio cholera* antigens.

In a preferred embodiment of the invention, DNA sequences obtained from a genomic library are inserted into the vector constructs of the present invention so that the genomic library may be screened for possible protective antigens. Non-limiting examples of genomic libraries which can be screened using the vector constructs of the present invention include, but are not limited to *Mycoplasma pulmonis* libraries, *Mycobacterium tuberculosis* libraries, and *Mycobacterium bovis* BCG libraries.

For assembly of the construct, the intein is inserted into a DNA sequence encoding a selectable marker. The intein may be positioned at any point within the selectable marker DNA sequence. Examples of DNA sequences encoding selectable markers that may be employed in the vectors of present invention include, but are not limited to thymidine kinase, encoded by the cellular, herpes simplex virus, or vaccine virus thymidine kinase genes; adenine phosphoribosyltransferase, encoded by the APTR gene; hypoxanthine-guanine phosphoribosyltransferase, encoded by the hgprt gene; aspartate transcarbamylase, encoded by the pyrB gene; ornithine decarboxylase, encoded by the odc gene; aminoglycoside phosphotransferase, encoded by the aph gene; hygromycin-B-phosphotransferase, encoded by the hph gene; xanthine-guanine phosphoribosyltransferase, encoded by the gpt gene; tryptophan synthetase, encoded by the trpB gene; histidinol dehydrogenase, encoded by the hisD gene; multiple drug resistance, encoded by the mdrl gene; dihydrofolate reductase, encoded by the dhfr gene; CAD (carbamyl phosphate synthetase, aspartate transcarbamylase, and dihydroorotase), encoded by the cad gene; adenosine deaminase, encoded by the ada gene; asparagine synthetase, encoded by the as gene; and glutamine synthetase, encoded by the gs gene. The preferred selectable marker for use in the vector constructs of the present invention is the aph gene, which confers resistance to kanamycin. Thus, if open reading frame DNA sequences, or DNA sequences that lack stop codons and frame shifts are inserted within the intein, protein splicing should not be affected, leading to production of aph gene product and kanamycin resistance.

The selectable marker may be part of an existing vector, or it may be inserted into a vector. Examples of suitable vectors into which the selectable marker may be inserted or found include, but are not limited to, pYUB53, pBR322, pUC18, pUC19, pHSV-106, pJS97, pJS98, M13mp18, M13mp19, pSPORT 1, pGem, pSPORT 2, pSV.SPORT 1, pBluescript II, λZapII, λgt10, λgt11, λgt22A, and λZIPLOX. Other suitable vectors are obvious to one skilled in the art. In a preferred embodiment of the present invention, the intein is inserted into the unique SspI site of the kanamycin resistance gene aph of an *E. coli*-mycobacteria shuttle vector pYUB53.

The vector constructs may also contain, in addition to a selectable marker, one or more additional expressible and selectable genes of interest. In a preferred embodiment of the invention, in addition to the aph gene encoding kanamycin resistance, the vector constructs contain a gene encoding tetracycline resistance. The tetracycline resistance gene allows for recombinant bacteria to be maintained in media containing tetracycline without applying any selective pressure on the manipulated aph gene and its product. Other examples of selectable markers that may be employed include, but are not limited to, the chloramphenicol resistance gene, tetracycline resistance gene, hygromycin resistance gene, geneticin resistance gene, B-galactosidase gene, ampicillin resistance gene, herpes simplex virus gene, vaccine virus thymidine kinase gene, adenine phosphoribosyltransferase gene, hypoxanthine-guanine phosphoribosyltransferase gene, aspartate transcarbamylase gene, ornithine decarboxylase gene, aminoglycoside phosphotransferase gene, hygromycin-B-phosphotransferase gene, xanthine-guanine phosphoribosyltransferase gene, tryptophan synthetase gene, histidinol dehydrogenase gene, multiple drug resistance gene, dihydrofolate reductase gene, CAD (carbamyl phosphate synthetase, aspartate transcarbamylase, and dihydroorotase) gene, adenosine deaminase gene, asparagine synthetase gene, and glutamine synthetase gene.

The vector constructs of the present invention also contain a nucleotide sequence encoding suitable regulatory elements so as to effect expression of the vector construct in a suitable host cell. Those skilled in the art will appreciate that a variety of enhancers, promoters, and genes are suitable for use in the constructs of the invention, and that the constructs will contain the necessary start, termination, and control sequences for proper transcription and processing of the selectable marker gene, DNA sequence encoding the intein, and the DNA sequence of interest, when the vector construct is introduced into a host cell. Suitable promoters include, but are not limited to, mycobacterial promoters, such as HSP60 and HSP70 promoters of *M. bovis*-BCG, mycobactin and a-antigen promoters of *M. bovis*-BCG and *M. tuberculosis*, the L1 and L5 mycobacteriophage promoters, and *E. coli* promoters such as ColE1.

Further, the DNA construct comprising the DNA sequence encoding the intein, splicing sequences, and the selectable marker may be inserted or assembled within a vector or a plasmid, as mentioned above. The construct can be assembled or spliced into any suitable vector or cosmid for insertion of a DNA of interest and incorporation into a suitable host cell.

The present invention also provides for a method of determining if a particular DNA of interest is an open reading frame DNA sequence. This method requires the use of the novel vector constructs of the present invention into which a DNA of interest is inserted. The vector constructs of the present invention contain a unique restriction site positioned within the DNA sequence encoding the intein into which a DNA of interest is inserted. The restriction site may be inserted into the DNA sequence encoding the intein, or it may be an existing restriction site within the DNA sequence encoding the intein.

As used herein, the DNA of interest inserted into the vector constructs may be any DNA sequence, coding or non-coding, open reading frame or non-open reading frame. As used herein, an open reading frame is a DNA sequence that is transcribed continuously into mRNA, and then translated continuously into an amino acid sequence, uninterrupted by stop codons. The translated open reading frame may be all or a portion of a gene encoding a protein or polypeptide.

The method provided by this invention specifically comprises the steps of inserting a DNA of interest into a unique restriction site positioned in the DNA sequence encoding the intein of the vector construct of the present invention, introducing said vector into a suitable host cell, growing the host cell for expression of the vector construct, and treating the host cell with the drug appropriate for the selective survival of the cell. Examples of drugs appropriate for the selective survival of the host cell include, but are not limited to, kanamycin, tetracycline, gentamycin, chloramphenicol and ampicillin. A host cell that grows in the presence of the appropriate drug for which the selectable marker confers resistance indicates that the intein has been spliced from the precursor protein and has restored the selectable marker so that the host cell exhibits resistance to the drug. Complete splicing of the intein from the precursor protein indicates that the DNA sequence encoding the intein within which the DNA of interest has been inserted has been transcribed continuously, further indicating that the DNA of interest is an open reading frame.

In a preferred embodiment of the invention, this method may be used for the detection and identification of open reading frame DNA sequences within a genomic DNA library, leading to the identification of potentially protective antigens of pathogenic organisms. Particular antigens which may be identified by the methods of the present invention include, but are not limited to, *Mycobacterium leprae* antigens, *Mycobacterium tuberculosis* antigens, *Mycoplasma pulmonis* antigens, *Mycobacterium bovis* BCG antigens, Rickettsia antigens, malaria sporozoites and merozoites, diptheria toxoids, tetanus toxoids, Clostridium antigens, Leishmania antigens, Salmonella antigens, Borrelia antigens, *Mycobacterium africanum* antigens, *Mycobacterium avium* antigens, *Mycobacterium intracellulare* antigens, Treponema antigens, Pertussis antigens, Schistosoma antigens, Filaria antigens, Herpes virus antigens, Shigella antigens, Neiserria antigens, rabies antigens, polio virus antigens, Rift Valley Fever virus antigens, dengue virus antigens, human immunodeficiency virus antigens, respiratory syncytial virus antigens, snake venom antigens, and *Vibrio cholera* antigens.

The vector constructs of the present invention can exist in integrated or unintegrated form within the host cell and are capable of autonomous replication when in unintegrated form. The term "host cell" as used herein means the bacterial or eukaryotic cell into which the vector is introduced. As used herein, "introduced" is a general term indicating that one of a variety of means has been used to allow the vector to enter the intracellular environment of the host cell in such a way that it exists in stable form therein.

It is to be understood that any one of a number of suitable bacterial or eukaryotic host cells can be transformed with the vector constructs of the present invention and utilized as expression or vaccine vehicles. Examples of suitable host cells are known to one skilled in the art and include, but are not limited to, *Escherichia coli, Salmonella typhimurium, Salmonella enteridis, Shigella dysenteriae, Shigella flexneri, Shigella sonnei, Mycobacterium bovis*-BCG, *Mycobacterium smegmatis, Mycobacterium tuberculosis, Mycobacterium avium, Mycobacterium phlei*, and *Mycobacterium intracellulare*. In a preferred embodiment of the invention, the vector constructs are introduced into *E. coli* and *M. smegmatis*. Examples of specific strains that may be used include, but are not limited to, *E. coli* strains DH5alpha, STABL-2, c600, c600hfl, HB101, LE392, Y1090, JM103, JM109, JM101, JM107, Y1088, Y1089, Y1090, Y1090(ZZ), DM1, PH10B, DH11S, DH125, RR1, TB1 and SURE, *Bacillus subtilis, Agrobacterium tumefaciens, Bacillus megaterium*; and eukaryotic cells such as *Pichia pastoris, Chlamydomonas reinhardtii, Cryptococcus neofornans, Neurospora crassa, Podospora anserina, Saccharomyces cerevisiae, Saccharomyces pombe, Uncinula necator*, cultured insect cells, cultured chicken fibroblasts, cultured hamster cells, cultured human cells such as HT1080, MCF7, 143B and cultured mouse cells such as EL4 and NIH3T3 cells.

The constructs may be introduced into host cells by a variety of gene transfer methods known to those skilled in the art, such as electroporation, treatment with calcium chloride, DEAE dextran, cationic liposome fusion, protoplast fusion, DNA coated-microprojectile bombardment, and infection with recombinant replication-defective retroviruses. Other techniques will be obvious to one skilled in the art. The term "transformation" will be used herein as a general term to denote the introduction of vector into a bacterial or eukaryotic host cell. As such, it encompasses transformation of bacterial cells and transfection, transduction and related methods in eukaryotic cells.

Expression of the host cell may be controlled and affected by the particular vector into which the DNA encoding the intein has been introduced. Some bacterial and eukaryotic vectors have been engineered so that they are capable of expressing inserted nucleic acids to high levels within the host cell. Such vectors utilize one of a number of powerful promoters to direct the high level of expression. For example, in vectors for the expression of a gene in a bacterial host cell such as *E.coli*, the lac operator-promoter or the tac promoter are often used. Eukaryotic vectors use promoter-enhancer sequences of viral genes, especially those of tumor viruses. Expression can be controlled in both bacterial and eukaryotic cells using inducible promoters such as the lac operator-promoter in *E. coli* or metallothionine or mouse mammary tumor virus promoters in eukaryotic cells. As used herein, "expression" refers to the ability of the vector to transcribe the inserted nucleic acid into mRNA so that synthesis of the protein encoded by the inserted nucleic acid can occur.

In a preferred embodiment of the invention, the host cell containing the vector construct of the present invention is maintained in the presence of tetracycline, and host cells containing a vector construct having a DNA of interest are selected for by treating the host cells with kanamycin.

The present invention provides for the use of a host cell of the present invention containing a vector construct having a DNA of interest as a DNA vaccine. The present invention also provides for the transformation of these host cells into vaccine vectors. In a preferred embodiment of the invention, the host cell is transformed into *M. bovis*-BCG. Employing recombinant *M. bovis*-BCG as live carrier provides an easy way to identify individual protective antigens, because after immunization and challenge, protected animals could be sacrificed to recover the responsible recombinant *M. bovis*-BCG organisms. The relevant inserted open reading frames could then be sequenced, and the protective antigen or antigens identified.

The vaccines of the present invention may be selected from, but not limited to, the group of mycobacterial species consisting of *M. smegmatis, M. bovis*-BCG, *M. avium, M. phlei, M. fortuitum, M. lufu, M. tuberculosis, M. leprae, M. habana, M. scrofulaceum*, and *M. intracellulare*. The recombinant bacterial vaccines of the present invention may be administered to immunize individuals against diseases such as tuberculosis, leprosy, malaria, diptheria, tetanus, leishmania, salmonella, schistomiasis, measles, mumps, herpes, and influenza. Administration of the recombinant mycobacterial vaccine to a host results in stimulation of the host's immune system to produce a protective immune response.

To form a vaccine, the recombinant bacteria of the present invention are administered in conjunction with a suitable pharmaceutical carrier. Representative examples of suitable carriers include, but are not limited to, mineral oil, alum, and synthetic polymers. Vehicles for vaccines are well known in the art and the selection of a suitable vehicle is deemed to be within the scope of those skilled in the art from the teachings contained herein. The selection of a suitable vehicle is also dependent on the manner in which the vaccine is to be administered. The vaccine may be in the form of an injectable dose, and may be administered intramuscularly, intravenously, orally, intradermally, intranasally, or subcutaneous administration.

The vector constructs and methods of using the constructs of the present invention utilize the unique protein splicing properties of inteins. The constructs and methods of the present invention are based on the premise that, if DNA sequences that lack stop codons and frame shifts are inserted within the intein, protein splicing should not be affected, leading to production of a selectable marker gene product which allows for selection of specific recombinants. In contrast, every stop codon or frame shift produces short truncated fusion proteins or non-splicable precursor proteins, resulting in a lack of production of the gene product of the selectable marker gene, and would thus identify those recombinants not of interest.

The vector constructs and methods of using the constructs of the present invention represent a novel approach for the identification of potentially protective antigens of a pathogen by using the vector constructs to select for whole or partial open reading frames from a genomic library of that organism. In contrast to a library of randomly cloned genetic material, a library of the vector constructs of this invention would represent most of the genes of a pathogen and very little non-coding sequences. The number of clones that would have to be analyzed in experimental animal models would therefore be dramatically reduced.

The present invention is described in the following Experimental Details Section, which is set forth to aid in an understanding of the invention, and should not be construed to limit in any way the invention as defined in the claims which follow thereafter.

Experimental Details Section

A. Materials and Methods

Construction of plasmids. Table 1 sets forth a list of plasmids used in these experiments and their descriptions. The M. tuberculosis recA intein was amplified from chromosomal DNA of the Erdman strain (generously provided by Amanda Brown), using the polymerase chain reaction (PCR). The primer pair P1 (5'-TGCCTCGCAGAGGGCACT) (SEQ ID NO: 1) and P2 (5'-ACAGTTGTGCACGACAACC) (SEQ ID NO: 2) was used to amplify a blunt end fragment containing the M. tuberculosis recA intein which was then used to construct plasmids pYUB750 and pYUB751. In a similar fashion, the primer pair P1 and P2a (5'-GTTGTGCACGACAACCCCT) (SEQ ID NO: 3) was used to construct plasmids pYUB752 and pYUB753, primer pair P1a (5'-CTCGCAGAGGGCACTCGG) (SEQ ID NO: 4) and P2 was used to construct plasmids pYUB754 and pYUB755, and primer pair P1a and P2a was used to construct plasmids pYUB756 and pYUB757. PCR was performed using Vent polymerase (New England Biolabs, Beverly, Mass.) which generates mostly blunt ended DNA fragments. PCR products were purified with Qiaquick spin columns (QIAGEN, Chatsworth, Calif.) and blunt end cloned into the unique SspI site of the kanamycin resistance gene aph of an E. coli-mycobacteria shuttle vector, pYUB53. DNA was ligated overnight with T4 DNA polymerase (Boehringer Mannheim, Indianapolis, Ind.), and transformed into E. coli DH5 alpha (Gibco BRL, Gaithersburg, Md.). E. coli transformants were grown on LB agar plates (Difco Laboratories, Detroit, Mich.) containing 12.5 µg per ml tetracycline (Tet; Sigma Chemical Co., St. Louis, Mo.). Plasmid DNA was isolated by conventional minipreps, and orientation of inserts was analyzed by restriction digest with PinAI (isoschizomer of AgeI; Boehringer Mannheim). To confirm correct insertion of the M. tuberculosis recA intein, junctions were sequenced using primers P27 (5'-GCGATCGCTGTTAAAAGGAC) (SEQ ID NO:5) or P28 (5'-GTTACTCACCACTGCGATCC) (SEQ ID NO:6). Sequencing reactions were performed using a dye terminator cycle sequencing kit (Perkin Elmer-ABI, Foster City, Calif.) and analyzed on an ABI 377 automated sequencer.

TABLE 1

| Plasmid | Description |
| --- | --- |
| pYUB53 | Kan[, TGt[, E.coli-mycobacteria shuttle vector, contains both ColE1 and OriM origins |
| pYUB56 | pYUB53 lacking a 1,449 bp Pst I fragment containing aph, religated, Tet[ |
| pYUB750 | M. tuberculosis recA intein including the C-terminal cystein codon was blunt-end cloned into the SspI site of aph in pYUB53, forward orientation |
| pYUB751 | same as pYUB750, but insert in reverse orientation |
| pYUB752 | M. tuberculosis recA intein without the C-terminal cystein codon was blunt-end cloned into the SspI site of aph in pYUB53, forward orientation |
| pYUB753 | same as pYUB750, but insert in reverse orientation |
| pYUB754 | M. tuberculosis recA intein including the C-terminal cystein codon-but lacking the N-terminal cystein codon-was blunt-end cloned into the SspI site of aph in pYUB53, forward orientation |
| pYUB755 | same as pYUB754, but insert in reverse orientation |
| pYUB756 | M. tuberculosis recA intein lacking both the N- and the C-terminal cystein codons was blunt-end cloned into the SspI site of aph in pYUB53, forward orientation |
| pYUB757 | same as pYUB756, but insert in reverse orientation |
| pYUB758 | pYUB750 lacking a 2,447 bp BsaAI fragment, religated. This plasmid cannot replicate in mycobacteria. |
| pYUB759 | pYUB758 with a BgI II site inserted into the M. tuberculosis recA intein at bp 102 |
| pYUB763 | pYUB758 with a BgI II site inserted into the M. tuberculosis recA intein at bp 510 |
| pYUB764 | pYUB758 with a BgI II site inserted into the M. tuberculosis recA intein at bp 612 |
| pYUB763::HA | pYUB763 containing the influenza virus hemagglutinin (HA) epitope inserted into the BgI II site |

Determination of protein splicing frequencies in E. coli. Transformed E. coli DH5 alpha were grown in LB medium containing 12.5 µg per ml Tet overnight. Serial tenfold dilutions were spotted (100 µl) on LB agar plates containing 35 µg per ml kanamycin (Kan; Sigma) or 12.5 µg per ml Tet. Plates were allowed to dry, incubated at 37° C. for 24 hrs, and then transferred to 30° C. for 3 days. Colony forming units (CFU) were counted and the ratio of Kan$^r$ CFU compared to Tet$^r$ CFU was determined.

Determination of protein splicing in Mycobacterium smegmatis. Plasmids pYUB53, pYUB750, pYUB751, pYUB752, and pYUB753 were electroporated into M. smegmatis (strain mc2155), as described previously (Snapper, et al., Proc. Natl. Acad. Sci. USA. 85:6987–6991 (1988)). Transformants were grown in Middlebrook 7H9 broth (Difco) supplemented with 10% albumin-dextrose-saline (ADS), 0.2% glycerol, 50 µg per ml cycloheximide (Sigma), 0.05% Tween 80 (Sigma) and 2.5 µg per ml Tet for 2 to 3 days at 37° C. Serial tenfold dilutions in Middlebrook 7H9 medium were (100 µg) on Middlebrook 7H10 agar plates (Difco) supplemented with 10% ADS, 0.5% glycerol, 50 µg per ml cycloheximide, and 2.5 µg per ml Tet or 20 µg per ml Kan. Plates were incubated for 3 days at 30° C., CFU were counted and the ratio of Kan$^r$ CFU compared to Tet$^r$ CFU was determined.

Metabolic labeling of protein synthesis in E. coli minicells. E. coli strain P678-54 carrying the minB-2 mutation (Adler, et al., Proc. Natl. Acad. Sci. USA. 57:321–326 (1967)) was obtained from the E. coli Genetic Stock Center (New Haven, Conn.). Bacteria were grown in LB medium, made chemo-competent by washing with calcium chloride, and transformed. Recombinant E. coli P678-54 were grown in LB broth with 12.5 µg per ml Tet overnight. The following morning, 10 ml fresh LB broth with Tet was inoculated 1:50 with overnight cultures, and grown at 37° C. on a shaker to mid-log phase. In order to eliminate most of the large cells, ampicillin (100 mg per ml, Sigma) was added, and incubation was continued for 2 hrs. Cultures were centrifuged twice at low speed to pellet most of the large cells. Minicells were pelleted by spinning 15 min at 3000 rpm, and resuspended in M9 minimal medium (Gibco) supplemented with 1 mM MgSO4, 0.1 mM $CaCl^2$, 0.05% NaCl, 0.2% glucose, and 1 ng per ml thiamine (Sigma). Newly synthesized proteins were labelled with [$^{35}$S]-methionine (DuPont NEN, Boston, Mass.) for 15 min, and minicells were collected immediately afterwards by centrifugation for 10 min at 4° C. and 14,000 rpm. Cells were resuspended in 50 to 100 µg Laemmeli-buffer, and disrupted by boiling and vortexing for 2 min each. Incorporation of [$^{35}$S]-methionine was determined by measuring the amount of radioactivity contained in 1 µl of the lysate after precipitation of proteins with trichloroacetic acid. Minicell lysates (50,000 to 100,000 cpm per lane) were electrophoresed on 10% polyacrylamide gels, using [$^{14}$C]-labeled rainbow markers (Amersham Life Sciences, Cleveland, Ohio.) as molecular weight standards. Gels were fixed, treated with Amplify (Amersham) for 30 min, dried and exposed to X-ray films for 1 to 8 days.

Construction of plasmid pYUB758. Plasmid pYUB750 was digested with BsaAI, and religated. The resulting plasmid, pYUB758, had a 2,447 bp deletion which removed most of the oriM sequence, thus rendering transformed M. smegmatis unable to replicate (data not shown). As a consequence of the 2,447 bp BsaAI deletion, plasmid pYUB758 was no longer cleavable by Bgl II.

Bgl II linker scanning mutagenesis of the M. tuberculosis recA intein. A Bgl II restriction site was inserted in frame into different positions within the M. tuberculosis recA intein in aph of plasmid pYUB758, using long-range PCR (LR-PCR). Primers of 30 bases length were designed with 21 bases homologous to the intein at position 102 from the start P21 (5'-ggaagatctGCCAAGGACGGAACGCTGCAT (SEQ ID NO:7); P22 (5'-ggaagatctAGCAGCCACGACATGAATAGG) (SEQ ID NO:8)), position 510 (P35 5'-ggaagatctCGACCCGGTGAGCGCAACGGT (SEQ ID NO:9)); 36 (5'-ggaagatctATGAGCGATCGCGAGTGAGAT) (SEQ ID NO:10)), and position 612 P37 (5'-ggaagatctGACATCGCGGCCGACATTGTC (SEQ ID NO: 11)); P38 (5'-ggaagatctCGGCTCGAAGAACCAATTCGG) (SEQ ID NO:12)). The first 9 bases of each primer (lower case) represented the Bgl II restriction sequences with 3 additional bases added. LR-PCR was performed using Vent-polymerase (NEB), 50 nmol of plasmid template, 2 mM magnesium sulfate, and 40 pmol of each primer. DNA was amplified in the following cycles: one cycle of 5 min at 96° C., 30 cycles of 1 min at 95° C., 1 min at 65° C., 8 min at 72° C., 1 cycle of 10 min at 72° C., and one infinite cycle of 4° C. LR- PCR products were separated on a 0.7% agarose gel, the dominant 6.4 kb band cut out, and purified with the Qiaquick gel extraction kit (QIAGEN). DNA was digested with Bgl II, ligated overnight, and transformed into competent E. coli DH5 alpha. Recombinant bacteria were grown on LB agar plates with 12.5 μg per ml Tet. Insertion of a Bgl II restriction site at the desired places was confirmed by DNA sequencing, and double restriction digests with EcoRV and Bgl II.

Insertion of the influenza hemagglutinin epitope into plasniid pYUB763. Oligonucleotides HA-1 (5'-gatctTACCCATACGACGTCCCAGACTACGCTg) (SEQ ID NO:13) and HA-2 (5'-gatccGCGTAGTCTGGGACGTCGTATGGGTAa) (SEQ ID NO:14) were designed to encode the sense and the antisense strand for the influenza hemagglutinin (HA) epitope (Wilson, et al., Cell, 37:767–778 (1984)). The oligonucleotides had a Bgl II restriction site at the 5' end, a BamHI restriction site at the 3' end (lower case), and were synthesized with phosphorylated 5' ends. HA-1 and HA-2 were hybridized and cloned into the Bgl II digested and dephosphorylated plasmid pYUB763. Positive clones were identified by probing dot blots of bacterial lysates with mouse-anti HA monoclonal antibody 12CA5 (Boehringer Mannheim), followed by incubation with peroxidase coupled goat-anti-mouse antiserum (BioRad Laboratories, Hercules, Calif.) and visualized with the ECL kit (Amersham). Insertion of the HA epitope was confirmed by double restriction digest with Bgl II and AspI (Boehringer Mannheim), which released a 184 bp fragment, as well as by DNA sequencing.

Insertion of a mycobacteriophage L5 library into plasmid pYUB763. A shuttle phasmid, phAE41, was used as a source for mycobacteriophage L5 DNA (Udani, et al., unpublished data). The plasmid was propagated in E. coli DH5 alpha in LB broth containing 100 μg per ml ampicillin, and purified by Qiagen midipreps. phAE41 DNA was completely digested with Sau3AI (NEB) overnight, and cloned into the Bgl II digested and dephosphorylated plasmid pYUB763. The ligation reaction was transformed into E. coli DH5 alpha, and plated on LB agar plates containing 12.5 μg per ml Tetracycline. Replica prints of these original plates were performed on LB agar plates containing Tet (to maintain all colonies) or Kanamycin (to select for plasmids with inserted open reading frames). Plates with Kanamycin were incubated for 1 d at 37° C. and 3 days at 30° C. Kan$^r$ colonies were marked, and their Tet$^r$ counterparts patched on LB agar plates containing Kanamycin. Colonies that proved to be truly Kan$^r$ were analyzed for inserted DNA fragments by PCR using primers P33 (5'-GGAAGATCTCGGCTCGAAGAACCAATTCGG)(SEQ ID NO:15) and P38 (SEQ ID NO:12) (see Bgl II linker scanning). PCR products were purified with Qiaquick columns, and sequenced (using the same primers, P33 or P38). A number of Kan$^s$ colonies were analyzed in the same fashion and also sequenced.

B. Results

Construction of pYUB750, a plasmid containing the M. tuberculosis recA intein within the kanamycin resistance gene aph. In order to construct the selectable marker/intein, the Mycobacterium tuberculosis recA intein was inserted into a selectable marker, the kanamycin resistance gene aph, which enabled us to select for protein splicing events by plating bacteria on media containing Kan. An Escherichia coli-mycobacteria shuttle vector, pYUB53, was used as vector so that protein splicing could be analyzed in both E. coli and mycobacteria. The plasmid pYUB53 contains two markers, aph and a Tet resistance gene (FIG. 1). Recombinant bacteria could therefore be maintained in media containing Tet without applying any selective pressure on the manipulated aph gene and its products.

Figure 2:
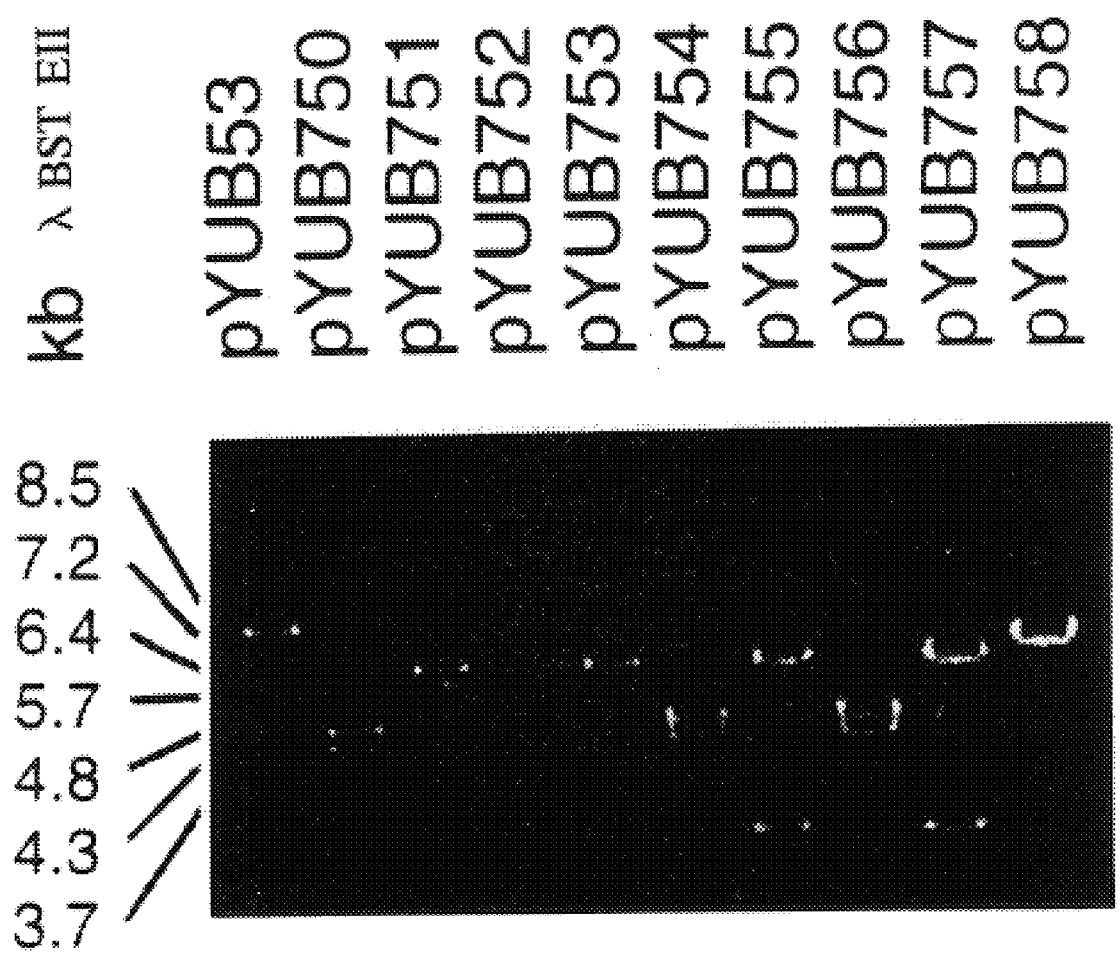
FIG. 2.

The M. tuberculosis recA intein was amplified blunt ended from chromosomal DNA by PCR, using a primer pair with homology to the N'- and C'-terminal splice sequences. To assure that the recombinant intein would be able to splice, the last C'-terminal cysteine codon—which was provided by the host gene recA was amplified together with the intein. This step was necessary because the cysteine residue is necessary for protein splicing but would not be provided by the aph gene at the intended insertion point. The resulting PCR products were blunt end cloned into the unique SspI site of the aph gene of pYUB53, which is located in the middle of the gene. Having the M. tuberculosis recA intein inserted in forward orientation, the plasmid was named pYUB750, in reverse orientation, the plasmid was named pYUB751 (FIG. 1). The orientation of the inserted M. tuberculosis recA intein was analyzed by restriction digest with PinAI, leading to a double band of 4.1 kb and 4.7 kb for pYUB750, and two bands of 2.9 kb and 5.9 kb for pYUB751 (FIG. 2). The junctions between aph and the M. tuberculosis recA intein were sequenced to ensure that no PCR errors had occurred (see Table 2).

TABLE 2

M. tuberculosis recA splice junctions in plasmids

| Plasmid | Length of insert | N'-splice junction | SEQ ID NO. | DNA sequence between junctions | C'-splice junction | SEQ ID NO. | expected gene product(s) |
|---|---|---|---|---|---|---|---|
| pYUB53 | none | ggtgaaaat | | none | attgttgat | | aph |
| pYUB750 | 1,323 bp | ggtgaaaatTGCC-TCGCAGAGG-GCACT | 16 | 1,287 bp, ORF | GTTGTCG-TGCACAA-CTGTattgttg-at | 17 | precursor, spliced intein, aph |
| | | CLAEGT | 18 | | VVVHN C | 19 | |
| pYUB751 | 1,323 bp | ggtgaaaatACAG-TTGTGCACG-ACAAC | 20 | 1287 bp, 3 stops | AGTGCCC-TCTGCGA-GGCAattgttg-at | 21 | precursor truncated at first stop codon |
| | | TVVHDN | 22 | | SALCEA | 23 | |
| pYUB752 | 1,320 bp | ggtgaaaatTGCC-TCGCAGAGG-GCACT | 24 | 1,287 bp, ORF | GTTGTCG-TGCACAA-Cattgttgat | 25 | precursor only, no spliced forms |
| | | CLAEGT | 26 | | VVVHN | 27 | |
| pYUB753 | 1,320 bp | ggtgaaaatGTTG-TGCACGACA-AC | 28 | 1,287 bp, 3 stops | AGTGCCC-TCTGCGA-GGCAattgttg-at | 29 | precursor truncated at first stop codon |
| | | VVHDN | 30 | | SALCEA | 31 | |
| pYUB754 | 1,320 bp | ggtgaaaatCTCG-CAGAGGGCA-CT | 32 | 1,287 bp, ORF | GGTGTCG-TGCACAA-CTGTatt-gttgat | 33 | precursor only, no spliced forms |
| | | LAEGT | 34 | | VVVHN C | 35 | |
| pYUB755 | 1,320 bp | ggtgaaaatACAG-TTGTGCACG-ACAAC | 36 | 1,287 bp, 3 stops | AGTGCCC-TCTGCGA-Gattgtt-gat | 37 | precursor truncated at first stop codon |
| | | TVVHDN | 38 | | SALCE | 39 | |
| pYUB756 | 1,317 bp | ggtgaaaatCTCG-CAGAGGGCA-CT | 40 | 1,287 bp, ORF | GTTGTCG-TGCACAA-Cattgttgat | 41 | precursor only, no spliced forms |
| | | LAEGT | 42 | | VVVHN | 43 | |
| pYUB757 | 1,317 bp | ggtgaaaatGTTG-TGCACGACA-AC | 44 | 1,287 bp, 3 stops | AGTGCCC-TCTGCGA-Gattgttgat | 45 | precursor truncated at first stop codon |
| | | VVHDN | 46 | | SALCE | 47 | |

Figure 3:
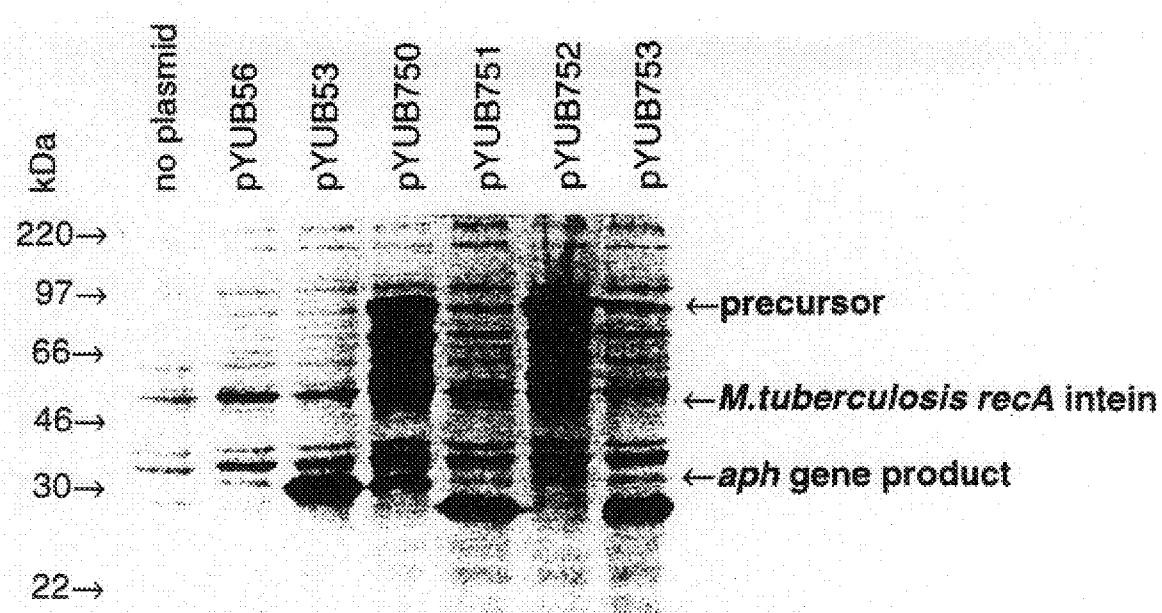
FIG. 3.

Recombinant E. coli cells carrying plasmid pYUB750 were expected to facilitate protein splicing of the M. tuberculosis recA intein out of the aph'-intein-aph' protein precursor (Table 2). Protein splicing would restore interrupted aph gene product, thus allowing the bacteria to grow on media containing Kan. In contrast, no protein splicing was expected for plasmid pYUB751 because three independent stop codons are encoded by the reverse intein, and the crucial amino acids at the N'- and C'-terminal splice sites could not be translated correctly because of altered codons (Table 2). Protein splicing was analyzed by growing recombinant E. coli and Mycobacterium smegmatis cells on media containing Kan. As expected, only plasmid pYUB750, but not plasmid pYUB751 rendered bacteria Kan$^r$ (see Table 3a, Table 3b). Metabolic labeling of newly synthesized proteins in an E. coli minicell strain (P678-54) further supported this hypothesis. This strain carries a minB-2 mutation which causes bacterial cells to divide asymmetrically (Adler at al., 1967). While large cells contain the entire chromosome, minicells have only plasmid DNA, so that enrichment for minicells allows to analyze for plasmid encoded gene products. FIG. 3 shows that the precursor protein (~80 kDa), the spliced out M. tuberculosis recA intein (47 kDa) and the aph gene product (30 kDa) appear in minicells transformed with pYUB750, but only small truncated fusion proteins of aph and the M. tuberculosis recA intein are formed in pYUB751 (presumably until translation reaches the first stop codon).

TABLE 3A

Protein splicing efficiency of basic constructs in E. coli

| Plasmid | Experiment | Tet[ CFU$^1$ | Kan[ CFU$^2$ | Frequency of Kan[ CFU |
|---|---|---|---|---|
| nil | 1 | n.d.$^3$ | 3.2 × 10$^2$/ml | n.a.$^4$ |
| | 2 | n.d. | 3.6 × 10$^2$/ml | n.a. |
| pYUB53 | 1 | 4.3 × 10$^8$/ml | 3.4 × 10$^8$/ml | 1/1.3 |
| | 2 | 1.1 × 10$^9$/ml | 1.3 × 10$^9$/ml | 1/1 |
| pYUB750 | 1 | 1.0 × 10$^7$/ml | 4.8 × 10$^4$/ml | 1/208 |
| | 2 | 1.3 × 10$^9$/ml | 1.9 × 10$^7$/ml | 1/68 |
| pYUB751 | 1 | 1.3 × 10$^8$/ml | 6.1 × 10$^2$/ml | 1/213,115 |
| pYUB752 | 1 | 1.0 × 10$^9$/ml | 4.1 × 10$^2$/ml | 1/2,439,024 |
| pYUB753 | 1 | 3.3 × 10$^8$/ml | 3.3 × 10$^2$/ml | 1/1,000,000 |
| pYUB754 | 1 | 1.6 × 10$^9$/ml | 6.0 × 10$^2$/ml | 1/266,667 |
| pYUB755 | 1 | 2.6 × 10$^8$/ml | 3.1 × 10$^2$/ml | 1/838,709 |
| pYUB756 | 1 | 2.7 × 10$^8$/ml | 4.8 × 10$^2$/ml | 1/562,500 |
| pYUB757 | 1 | 3.2 × 10$^8$/ml | 8.0 × 10$^1$/ml | 1/4,000,000 |

$^1$incubation for 1 d at 37° C.
$^2$incubation for 1 d at 37° C., plus 3-d at 30° C.
$^3$not done
$^4$not applicable

TABLE 3B

Protein splicing efficiency of basic constructs in M. smegmatis

| Plasmid | Experiment | Tet$^r$ CFU$^1$ | Kan$^r$ CFU$^1$ | Frequency of Kan$^r$ CFU |
|---------|------------|-----------------|-----------------|--------------------------|
| nil     | 1          | n.d.$^2$        | n.d             | n.a.$^3$                 |
|         | 2          | 0               | 0               | n.a.                     |
| pYUB53  | 1          | 1.2 × 10$^9$/ml | 1.5 × 10$^9$/ml | 1/1                      |
|         | 2          | 9.5 × 10$^8$/ml | 1.0 × 10$^9$/ml | 1/1                      |
| pYUB750 | 1          | 2.6 × 10$^9$/ml | 2.2 × 10$^9$/ml | 1/1.2                    |
|         | 2          | 7.4 × 10$^8$/ml | 1.1 × 10$^8$/ml | 1/7                      |
| pYUB751 | 1          | 9.8 × 10$^8$/ml | 0               | 0                        |
|         | 2          | 1.1 × 10$^9$/ml | 5.0 × 10$^0$/ml | 1/220,000,000            |
| pYUB752 | 1          | 1.7 × 10$^9$/ml | 1.0 × 10$^1$/ml | 1/170,000,000            |
|         | 2          | 7.8 × 10$^8$/ml | 3.0 × 10$^0$/ml | 1/260,000,000            |
| pYUB753 | 1          | 3.2 × 10$^8$/ml | 1.0 × 10$^1$/ml | 1/32,000,000             |
|         | 2          | 1.0 × 10$^9$/ml | 3.0 × 10$^0$/ml | 1/333,333333             |

$^1$incubation for 1 d at 37° C., plus 2 d at 30° C., plus 4 d at room temperature
$^2$not done
$^3$not applicable The role of individual amino acids at the N'- and C'-terminal hexapeptide splice sites of various inteins has been the focus of several studies (Davis, et al., *Cell*, 71:201–210 (1992), Hirata and Anraku, *Biochem. Biophys. Res. Comm.*, 188:40–47 (1992), Hodges, et al., *Nucleic Acids Research*, 20:6153–6157 (1992), Cooper et al., *EMBO Journal*, 12:2575–2583 (1993)). It has been shown that both the N'- and the C'-terminal cysteine residues are essential for protein splicing. Several constructs were made in order to confirm these results in the vector system, as well as to generate a number of control plasmids. The *M. tuberculosis* recA intein was amplified blunt ended from chromosomal DNA with the following modifications: (i) the last cysteine codon at the C' terminus was omitted; (ii) the initial cysteine codon at the N' terminus was omitted; (iii) both the initial and the last cysteine codon were omitted. All truncated *M. tuberculosis* recA intein PCR products were blunt end cloned into the unique SspI site of the aph gene of pYUB53. Plasmid pYUB752 contained the C' terminal cysteine truncated *M. tuberculosis* recA intein in forward orientation, and plasmid pYUB753 had a reverse insert (FIG. 1, Table 2). Plasmid pYUB754 contained the N' terminal cysteine truncated *M. tuberculosis* recA intein in forward orientation, and plasmid pYUB755 had a reverse insert (Table 2). Plasmid pYUB756 contained the double cysteine truncated *M. tuberculosis* recA intein in forward orientation, and plasmid pYUB757 had the reverse insert (Table 2). The orientation of the truncated *M. tuberculosis* recA intein sequences was analyzed by restriction digest with PinAI (FIG. 2), and confirmed by sequencing across the junctions (Table 2). As predicted (Table 2), none of the plasmids containing cysteine truncated inteins allowed protein splicing to occur in *E. coli* or *M. smegmatis* (see Tables 3a, 3b). Minicell analysis showed that plasmid pYUB752 encoded for a stable precursor protein which was unable to splice, whereas the plasmid with a reverse insert, pYUB753, generated only short truncated fusion proteins, just like pYUB751 (FIG. 3). Plasmids pYUB754 and pYUB756 produced precursor proteins similar to those seen with pYUB752, and plasmids pYUB755 and pYUB757 also gave rise to short truncated fusion proteins, like pYUB751 and pYUB753.

Genetic analysis of the *M. tuberculosis* recA intein by BgI II linker scanning mutagenesis. After creation of the construct, pYUB750, which contained the *M. tuberculosis* recA intein within a selectable marker, and after showing that protein splicing occurred in both *E. coli* and *M. smegmatis*, additional DNA sequences were then inserted into the *M. tuberculosis* recA intein, and successful splicing was analyzed by selecting for Kan$^r$ colonies. Since hardly anything is known about the protein structure of the *M. tuberculosis* recA intein, it could not be predicted where the optimal position for an insertion site would be. Also, very little is known about the optimal length of a DNA sequence to be inserted. Therefore, a linker scanning mutagenesis was performed, which is a genetic approach to analyze which parts of a protein represent essential and non-essential regions. The DNA sequence for a new BgI II restriction site (i.e. a linker) was inserted into different regions of the *M. tuberculosis* recA intein, thus generating mutated inteins which had an insertion of two extra amino acids, an arginine and a serine residue. This strategy should indicate whether the chosen site was essential (and would not even tolerate an insertion of two amino acids) or whether a non critical region of the intein was found.

Naturally, a targeted plasmid for linker scanning mutagenesis should not have the respective restriction sequence before manipulation. Plasmid pYUB750, however, had a BgI II site contained within the mycobacterial origin of replication (oriM) sequence. Since the inventors already knew that protein splicing worked equally well in *E. coli* and mycobacteria, a large part of the oriM sequence was removed, and protein expression in *E. coli* was focused on. Plasmid pYUB750 was digested with BsaAI and religated, yielding plasmid pYUB758 (FIG. 1). This 6.4 kb plasmid had a 2,447 bp deletion, and the remaining part of oriM was no longer able to allow replication of pYUB758 in *M. smegmatis* (data not shown). Protein splicing of the *M. tuberculosis* recA intein in *E. coli* was not affected, as shown by the number of Kan$^r$ colonies (Table 4).

TABLE 4

Protein splicing efficiency of plasmids with BgI II insertions in *E. coli*

| Plasmid     | Experiment | Tet$^r$ CFU$^1$    | Kan$^r$ CFU$^2$    | Frequency of Kan$^r$ CFU |
|-------------|------------|--------------------|--------------------|--------------------------|
| nil         | 1          | n.d.$^3$           | 3.2 × 10$^2$/ml    | n.a.$^4$                 |
|             | 2          | n.d.               | 3.6 × 10$^2$/ml    | n.a.                     |
| pYUB758     | 1          | 1.0 × 10$^7$/ml    | 5.6 × 10$^4$/ml    | 1/179                    |
|             | 2          | 1.1 × 10$^9$/ml    | 9.5 × 10$^6$/ml    | 1/116                    |
| pYUB759     | 1          | 3.0 × 10$^7$/ml    | 2.3 × 10$^2$/ml    | 1/130,434                |
| PYUB763     | 1          | 1.0 × 10$^7$/ml    | 4.7 × 10$^4$/ml    | 1/213                    |
|             | 2          | 8.0 × 10$^8$/ml    | 2.2 × 10$^7$/ml    | 1/36                     |
| pYUB764 #2  | 2          | 1.2 × 10$^9$/ml    | 2.5 × 10$^4$/ml    | 1/48,000                 |
| pYUB764 #4  | 2          | 7.0 × 10$^8$/ml    | 2.8 × 10$^4$/ml    | 1/25,000                 |
| pYUB764 #13 | 2          | 2.0 × 10$^9$/ml    | 7.7 × 10$^2$/ml    | 1/2,597,403              |
| pYUB764 #14 | 2          | 2.2 × 10$^9$/ml    | 3.5 × 10$^2$/ml    | 1/6,285,714              |
| pYUB764 #15 | 2          | 1.7 × 10$^9$/ml    | 3.1 × 10$^4$/ml    | 1/54,839                 |

Figure 4:
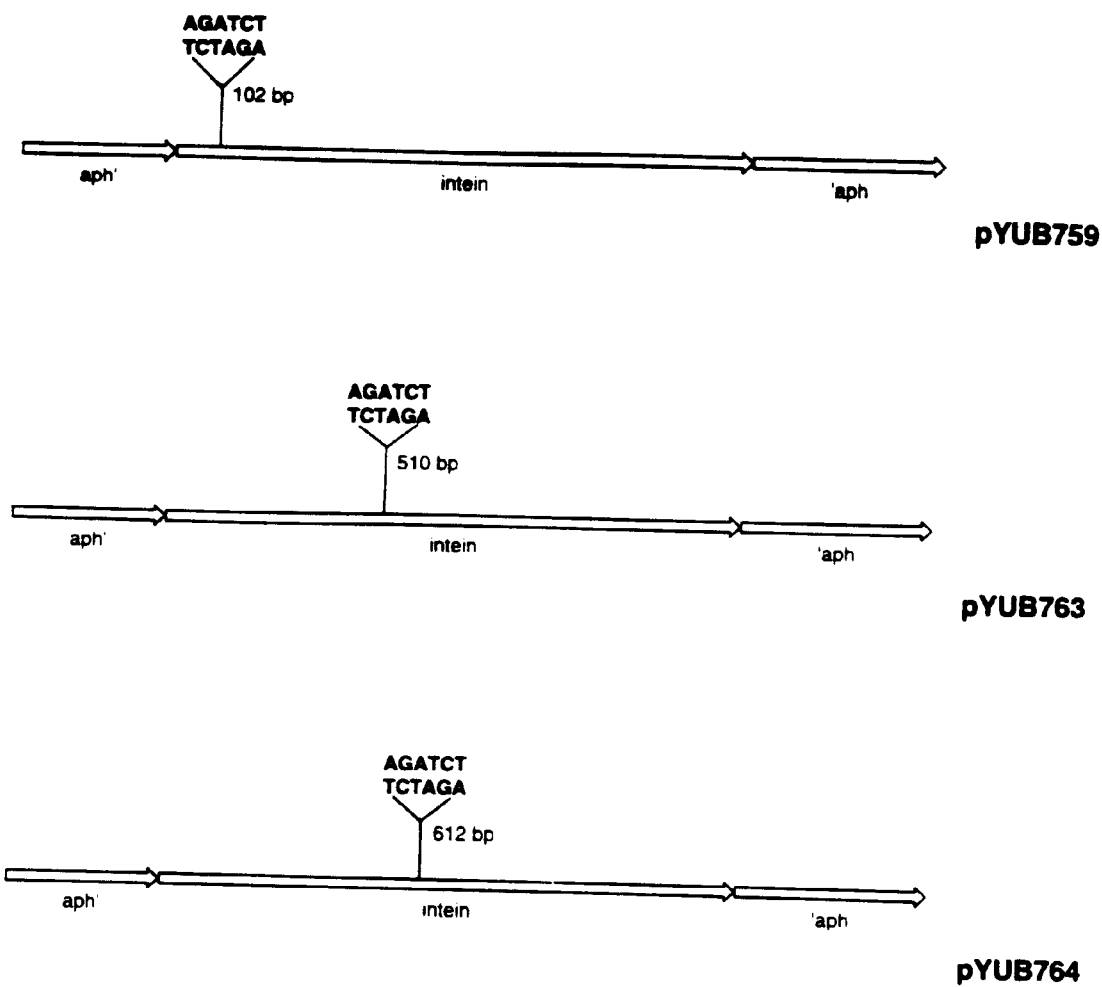
FIG. 4.
Figure 5:
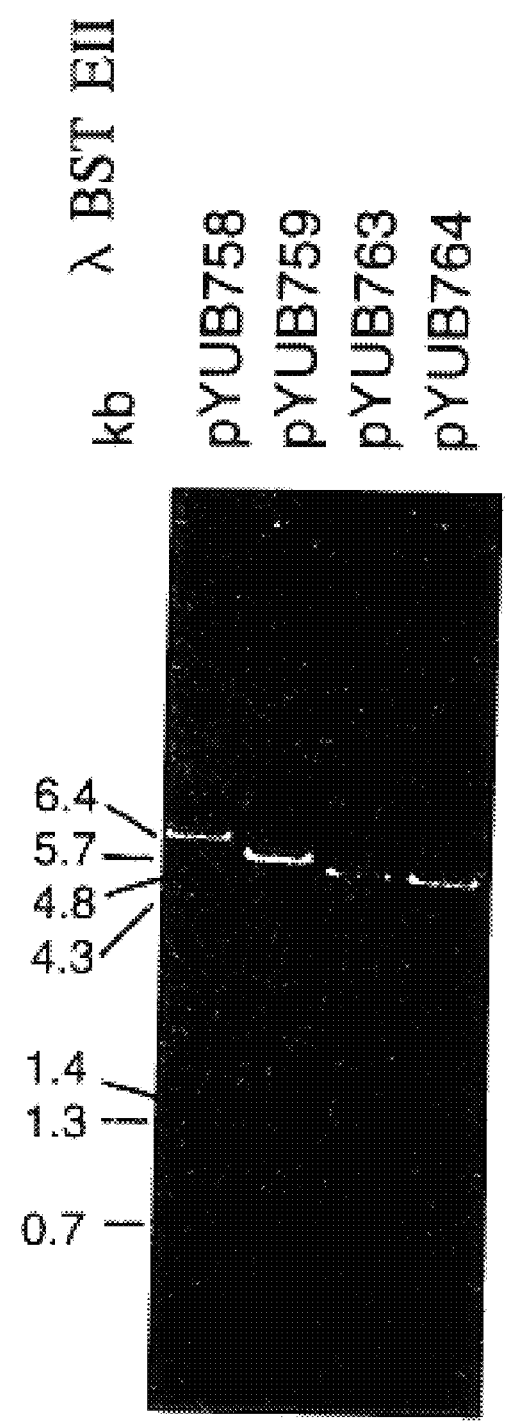
FIG. 5.

$^1$incubation for 1 d at 37° C.
$^2$incubation for 1 d at 37° C., plus 3 d at 30° C.
$^3$not done
$^4$not applicable The insertion of the BgI II restriction site was performed by long-range PCR (LR-PCR). Primers were designed with homology to the *M. tuberculosis* recA intein, initiating at the same point of the intein, but pointing into opposite directions. The complete plasmid was thereby amplified, yielding a linear 6.4 kb fragment. The primers had BgI II restriction sites at the 5' ends, so that the PCR products could be digested and religated. Using this strategy, three different constructs were generated: (i) plasmid pYUB759 which had a BgI II site inserted in frame 102 bp from the start of the intein, (ii) plasmid pYUB763 which had a BgI IL site inserted in frame 510 bp from the start, (iii) plasmid pYUB764 which had a BgI II site inserted in frame 612 bp from the start (FIG. 4). Insertion of the BgI II restriction sites and correct position was determined by double restriction digest with Bgl II and EcoRV, generating a characteristic pattern (1.0 and 5.4 kb for pYUB759; 1.4 and 4.9 kb for pYUB763; 1.5 and 4.8 kb for pYUB764; FIG. 5). DNA sequencing confirmed the correct insertion.

Analysis of the protein splicing frequencies of these three constructs gave some interesting results. Insertion of an arginine and a serine residue (which are encoded by the Bgl II sequence) into the *M. tuberculosis* recA intein 34 amino acids after the N' terminus (i.e. 102 bp from the start) almost completely inhibited protein splicing, whereas insertion of these two residues after 170 amino acids (i.e. 510 bp from the start) did not affect the splicing process at all (see Table 4). Insertion of an arginine and a serine residue into the *M. tuberculosis* recA intein after 204 amino acids (i.e. 612 bp from the start) gave us two types of clones, some of which did not tolerate the two extra amino acids (clone #13, and #14) and some that did, although with impaired splicing ability (clone #2, #4, and #15; Table 4).

Figure 6:
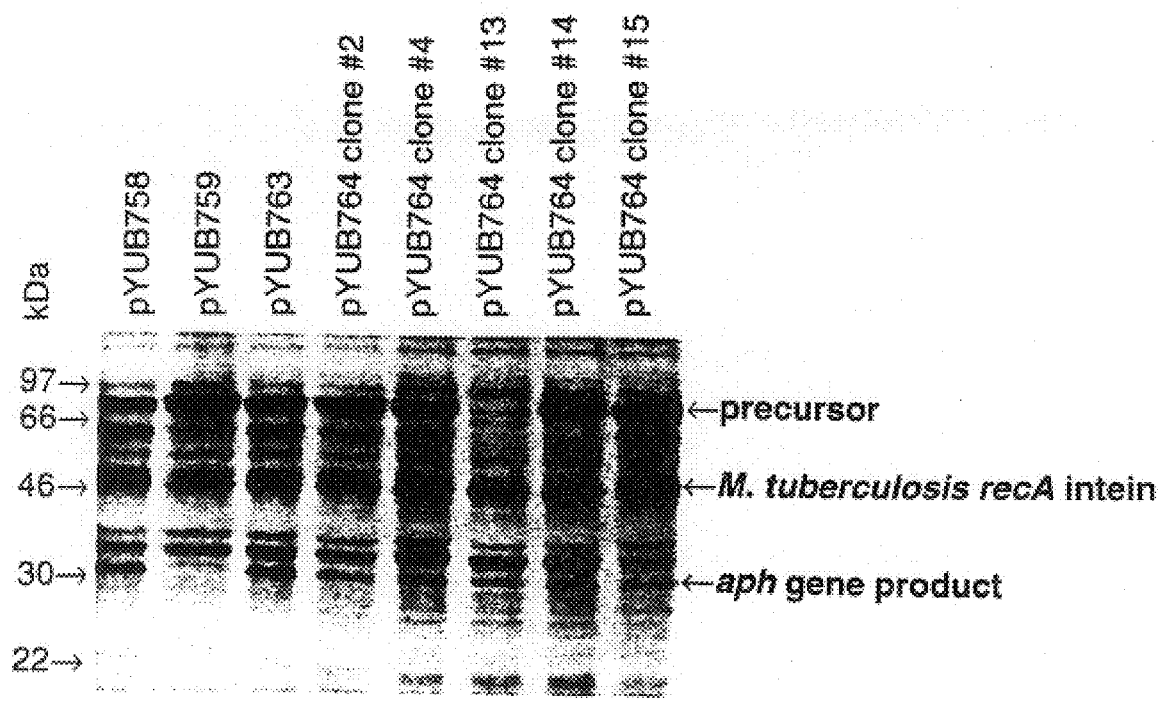
FIG. 6.

Minicell analysis demonstrated that plasmid pYUB759 generated only the precursor protein, whereas plasmid pYUB763 allowed protein splicing just as well as the unmanipulated vector pYUB758 (FIG. 6). In all 5 clones which were analyzed for plasmid pYUB764 the reconstituted aph band was clearly visible, but appeared fainter than in lysates from cells transformed with pYUB758 or pYUB763. pYUB764 clone #13 did not show a precursor protein band, which is very unusual. While these results explained the differences which were observed in splice frequencies for pYUB759 and pYUB763 (Table 4), they did not clarify the issue why some pYUB764 clones were Kan$^s$. Since the aph gene product was seen in all 5 pYUB764 clones, it seems likely that PCR errors were introduced into the aph sequence in clones #13 and #14, which consequently rendered spliced out aph gene product unable to confer Kan$^r$.

The ultimate goal was to generate a set of 12 different plasmids, each containing a Bgl II site in frame of the *M. tuberculosis* recA intein, thus analyzing the whole intein in increments of 102 bp. So far, only three constructs have been created, and the inventors could show that some regions of the *M. tuberculosis* recA intein are extremely sensitive to even a minute interruption, whereas others are more suitable for insertions.

Insertion of the influenza virus hemagglutinin (HA) epitope into the *M. tuberculosis* recA intein. The next step involved the determination of whether plasmid pYUB763 (which already has two extra amino acids introduced into the *M. tuberculosis* recA intein) would tolerate the insertion of an additional small peptide. A frequently used genetic marker was chosen, the influenza hemagglutinin (HA) tag as the test epitope because it is only 9 amino acid residues long and can be screened for with a commercially available monoclonal antibody (Wilson, et al., *Cell*, 37:767–778 (1984)).

Figure 7:
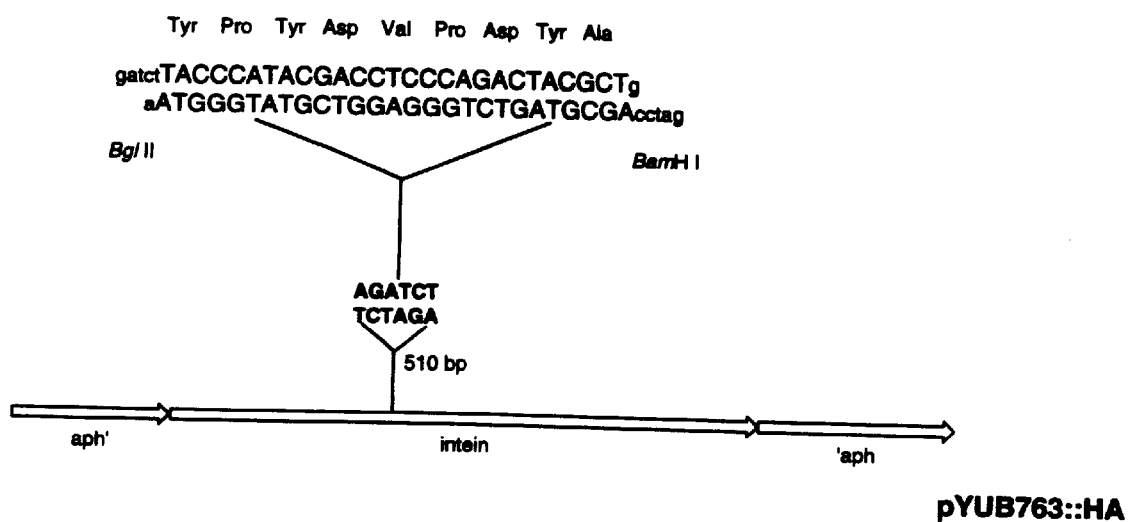
FIG. 7.

Oligonucleotides encoding for the sense and antisense strand of the HA tag were synthesized with additional restriction sites at each end. A Bgl II site was added to the 5' end, and a BamHI site to the 3' end (FIG. 7). After ligation of the HA tag to the Bgl II digested plasmid pYUB763, the unique Bgl II site would be retained at the 5' end of the HA tag, whereas a non-cleavable Bgl II/BamHI hybrid site would be formed at the 3' end (FIG. 7).

Figure 8:
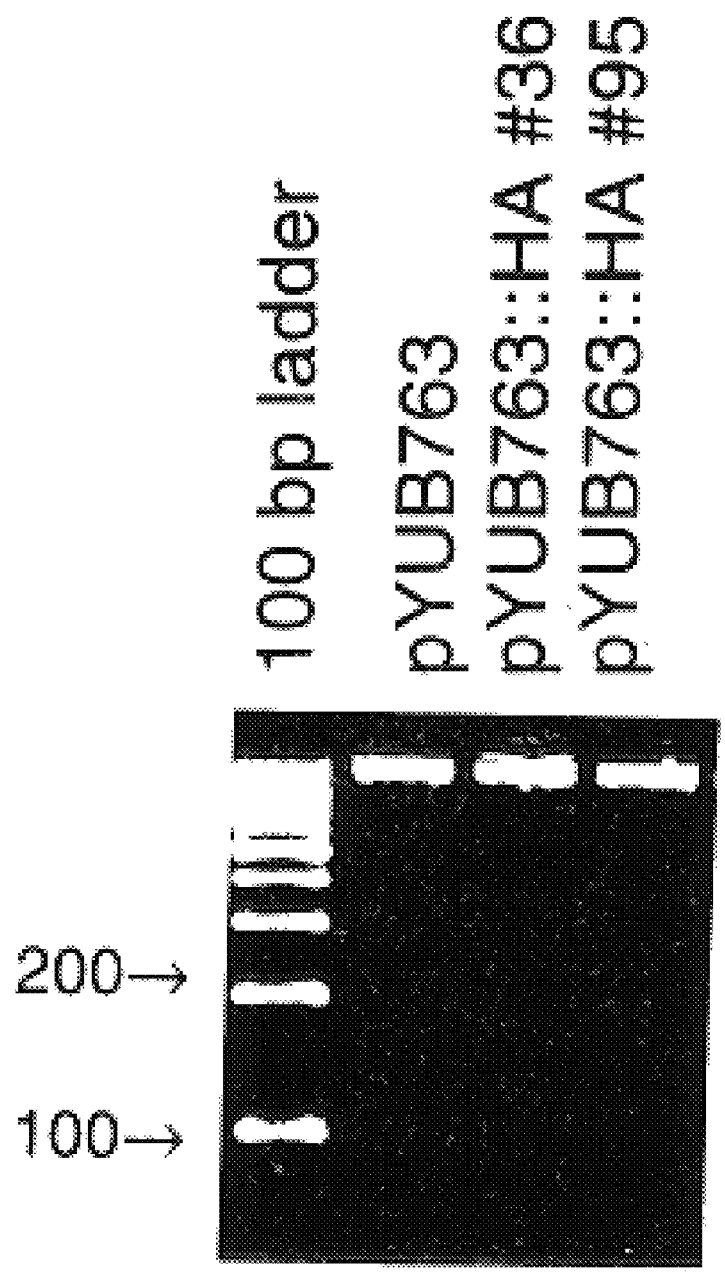
FIG. 8.

Two clones, pYUB763::HA #36, and pYUB763::HA #95 were identified by screening lysates of *E. coli* transformants in dot blots with a mouse monoclonal antibody, 12CA5 (data not shown). The presence of the HA tag within the *M. tuberculosis* recA intein was confirmed by double restriction digests with Bgl II and Aspl, which released a 151 bp fragment in plasmid pYUB763, whereas a 184 bp fragment was liberated in HA containing plasmids pYUB763::HA #36 and pYUB763::HA #95 (FIG. 8). Correct insertion of the HA epitope was validated by sequencing across the region.

Figure 9A:
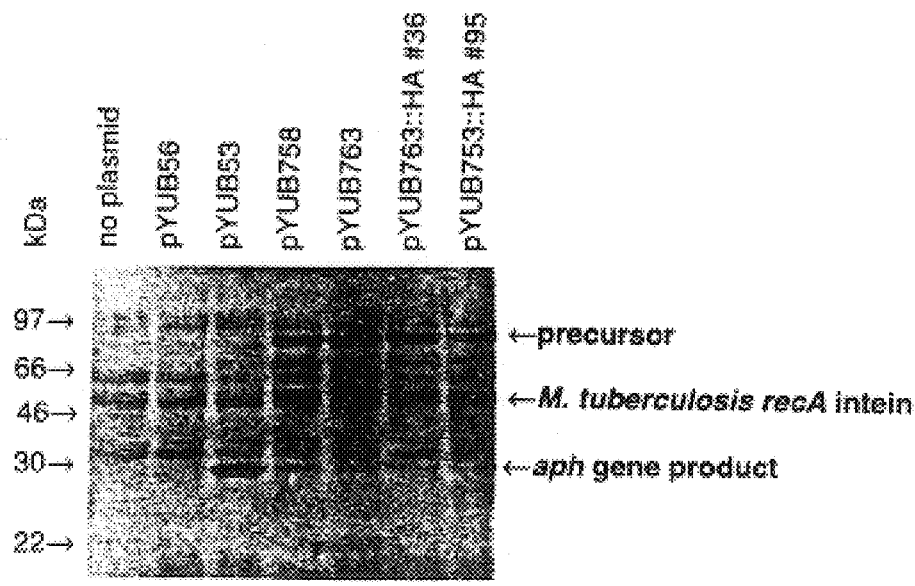
FIGS. 9A and 9B.
Figure 9B:
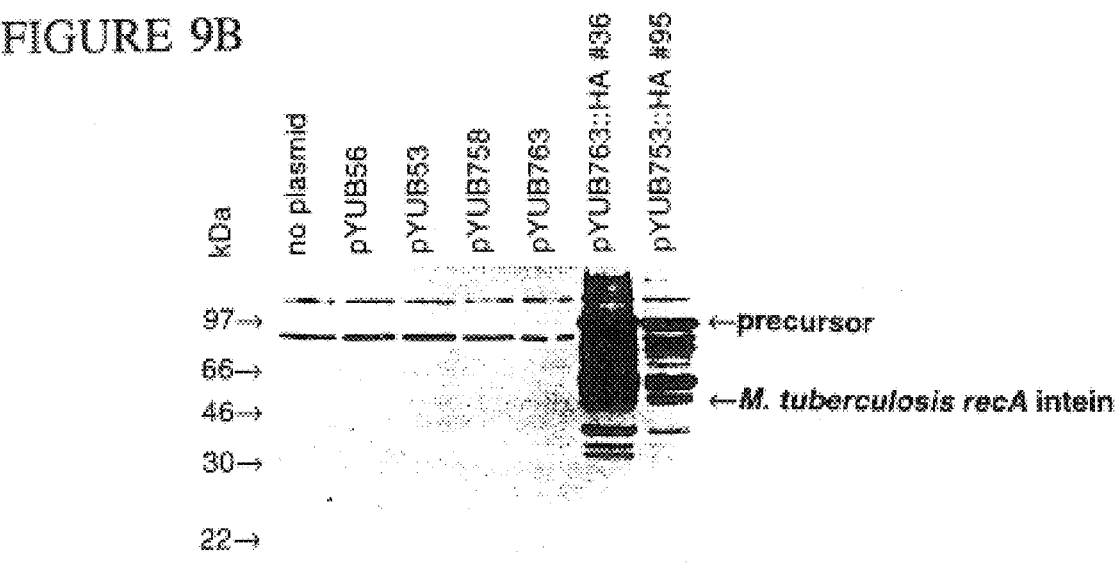

When *E. coli* transformants containing plasmids pYUB763::HA #36 or pYUB763::HA #95 were analyzed for Kan$^r$, they showed a high protein splicing frequency, almost reaching the levels conferred by the vector pYUB763. A minicell analysis confirmed our observations, showing that all splice forms, the precursor, the spliced out intein and the reconstituted aph gene product were translated in cells containing plasmids pYUB763::HA #36 or pYUB763::HA #95 (FIG. 9a). FIG. 9b shows a Western blot of the same polyacrylamide gel, and was developed using the anti-HA monoclonal antibody. HA-tagged protein are visible in minicells transformed with pYUB763::HA#36 and pYUB763::HA #95, but are not detected in transformants expressing the non-tagged *M. tuberculosis* recA intein. Using the anti-HA antibody, it was demonstrated that protein splicing did release the tagged intein protein and reconstituted the aph gene product. Apart from the precursor protein, several proteins of intermediate length were also detected by the antibody, thereby demonstrating the presence of intermediate splice forms, or/and potential degradation products. Splice forms of intermediate length have been observed in the splicing process of other inteins, and have been proposed to be part of the normal protein splicing mechanism (Xu, et al., *Cell*, 75:1371–1377 (1993); Xu, et al., *EMBO Journal*, 13:5517–5522 (1994)). At this step, however, the possibility cannot be ruled out that there may be internal start codons within the aph gene which would explain the presence of some of the shorter tagged proteins. To clarify this issue, the HA epitope was inserted into plasmid pYUB752 (which does not allow protein splicing to occur) in order to see whether the shorter proteins are caused by splicing or by internal starts.

The selection and identification of open reading frames: Construction of a genomic library of mycobacteriophage L5 in plasmid pYUB763. Thus, the inventors have shown that the region around position 510 bp of the *M. tuberculosis* recA intein was a useful site to insert DNA sequences into the intein gene, and that protein splicing would not be severely impaired by short inserts. Future analysis may reveal an even better site within the sequence of the *M. tuberculosis* recA intein, but presently, plasmid pYUB763 seemed a good candidate to attempt a first experiment for the identification of open reading frames.

Mycobacteriophage L5 was chosen as DNA donor because of its relatively small genome (52,297 bp) which has been completely sequenced (Hatfull and Sarkis, *Mol. Microbiol.*, 7:395–405 (1993)). L5 has 88 genes, 85 of them encode for proteins, and 3 encode for tRNAs (Hatfull and Sarkis, *Mol. Microbiol.*, 7:395–405 (1993)). A shuttle phasmid, phAE41, with a size of 50,341 bp was previously constructed (Udani, et al., unpublished data) and contains the full coding L5 genome in the context of an *E. coli* plasmid with an ampicillin resistance marker. Therefore, L5 DNA could then be propagated as a plasmid in *E. coli* and purify DNA by conventional methods. After the DNA preparation was shown to be nuclease free, it was completely digested with a frequent cutter, Sau3AI. A restriction map of phAE41 showed that the DNA would be cleaved 424 times, generating fragments ranging from 985 bp (maximal size) to 4 bp (minimal size; data not shown).

Figure 10:
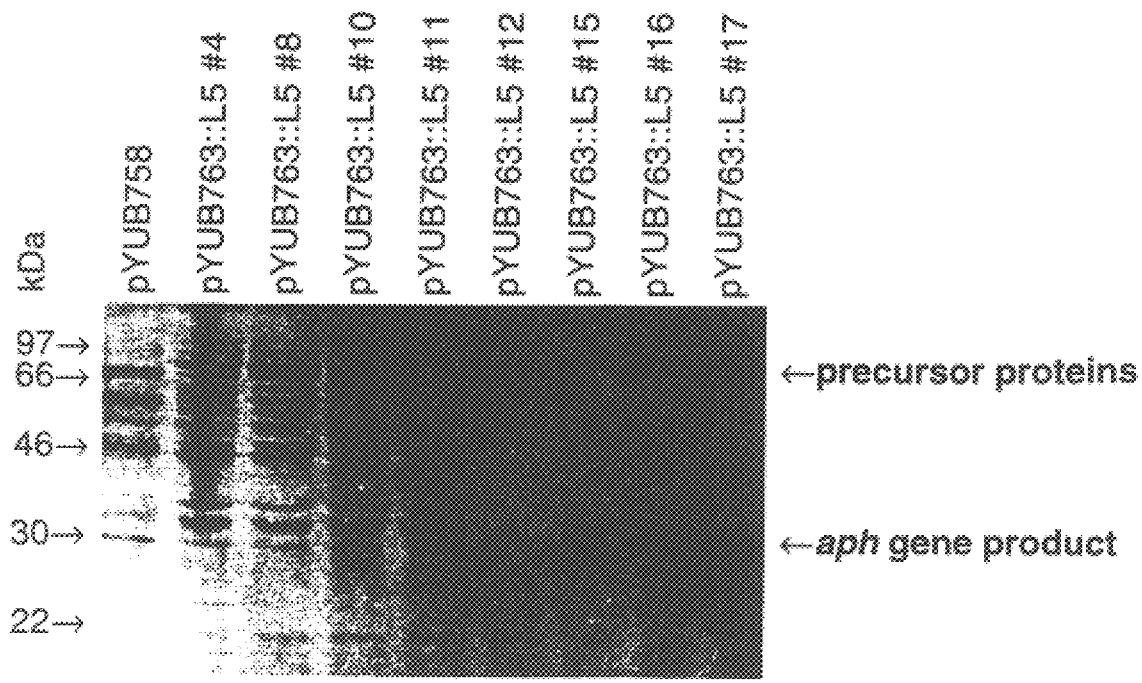
FIG. 10.
Figure 11:
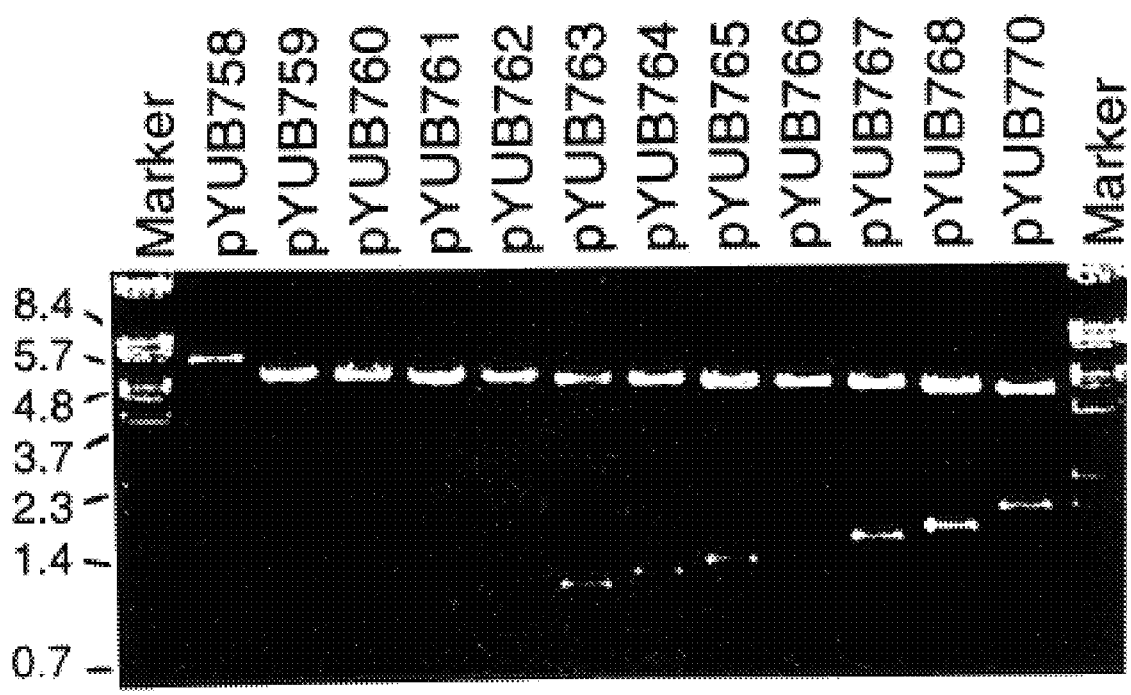
FIG. 11.

Plasmid pYUB763 was digested with Bgl II, and ligated to the DNA fragments generated in a phAE41 Sau3AI digest. E. coli transformants were selected on LB agar plates containing Tet to ensure that every recombinant plasmid would be retained. The library of mycobacteriophage L5 in pYUB763 consisted of 5,000 clones, thus representing every fragment of the Sau3AI digest L5 approximately ten times (see Table 6). The background of empty vector plasmid which had religated without an insert was 5 to 6%. Colonies were replica printed onto LB plates containing Tet or Kan. 19 Kan$^r$ clones were initially identified, but only 15 proved to be truly Kan$^r$ in a second streaking (Table 6). These 15 clones were subjected to PCR analysis, from which it could be demonstrated that 8 clones had inserts, while 7 represented empty vector plasmids (Table 6, PCR data not shown). The PCR products were then sequenced in order to see if the inserts were genuine open reading frames and to compare the sequence to the NIH database in a BLAST search. It could be shown that all 8 inserts had a high degree of homology to mycobacteriophage L5, and that all of them were in fact open reading frames (Table 7). Surprisingly, only four DNA fragments were inserted in forward orientation, whereas 2 were inserted reverse, yet not encoding for any stop codons. Two of the inserts represented concatamers of more than one Sau3AI L5 fragment that had formed before insertion into pYUB763. The insert in clone #17 consisted of 2 fragments, and the insert in clone #10 had as many as four components, but no frameshift was induced or stop codon formed. The smallest insert encoded for 10 amino acids (including the amino acids encoded by the restriction sites), the largest insert was as big as 62 amino acids. When the 8 plasmids with permissive inserts were analyzed for protein splicing frequencies in E. coli, seven out of eight clones spliced with equally high frequencies, and only clone #11 had a reduced splicing capacity (Table 8). Interestingly, this is the clone with the largest insert size. Minicell analysis of the newly synthesized proteins showed that the aph gene product is reconstituted in all eight pYUB763::L5 clones (FIG. 10). The precursor proteins show a slightly higher molecular weight than the precursor protein of pYUB763, which reflects the effect of the inserted mycobacteriophage L5 amino acids. Without a specific antibody to the M. tuberculosis recA intein, it is hard to identify the spliced out recombinant intein bands, but since the aph gene product and the enlarged precursor proteins are visible, it is evident that protein splicing has indeed been successful in all eight pYUB763::L5 clones.

Ten Kan$^s$ clones were analyzed in a similar fashion. All ten had inserts, ranging from 10 to 177 amino acids in length (Table 7). Sequencing analysis revealed that all but one insert matched to the mycobacteriophage L5 genome, and that all encoded for at least one stop codon, some had as many as six. Frameshifts were observed in four cases. The one insert which did not match to L5 showed a high degree of homology to beta-lactamase genes, and represented part of the ampicillin resistance gene of the plasmid part of phAE41.

It is therefore demonstrated by the data contained herein that it is possible to insert foreign DNA sequences into the M. tuberculosis recA intein while still allowing the intein to splice out of its host gene. By using a selectable marker, these rare events were identified, and 8 clones were found (representing 3% of the mycobacteriophage L5 library) that contained DNA fragments of open reading frames. The largest identified insert encoded for 62 amino acids, thereby increasing the size of the *M. tuberculosis* recA intein from 440 amino acids (47 kDa) to 502 amino acids (54 kDa).

TABLE 5

Protein splicing efficiency of plasmids containing the HA tag in *E. coli*

| Plasmid | Experiment | $Tet^r$ CFU[1] | $Kan^r$ CFU[2] | Frequency of $Kan^r$ CFU |
|---|---|---|---|---|
| nil | 1 | n.d.[3] | $3.2 \times 10^2$/ml | n.a.[4] |
| | 2 | n.d. | $3.6 \times 10^2$/ml | n.a. |
| pYUB763 | 1 | $1.0 \times 10^7$/ml | $4.7 \times 10^4$/ml | 1/213 |
| | 2 | $8.0 \times 10^8$/ml | $2.2 \times 10^7$/ml | 1/36 |
| pYUB763::HA #36 | 1 | $1.0 \times 10^7$/ml | $9.0 \times 10^3$/ml | 1/1,111 |
| | 2 | $1.3 \times 10^9$/ml | $5.0 \times 10^6$/ml | 1/260 |
| pYUB763::HA #95 | 1 | $1.0 \times 10^7$/ml | $6.8 \times 10^4$/ml | 1/147 |
| | 2 | $7.0 \times 10^8$/ml | $2.5 \times 10^6$/ml | 1/280 |

[1]incubation for 1 d at 37° C.
[2]incubation for 1 d at 37° C., plus 3 d at 30° C.
[3]not done
[4]not applicable

TABLE 6

Plasmid library of mycobacteriaphage L5 in pYUB763

| Library size | Analysed $Tet^r$ *E. coli* clones | CFU after replica printing: $Tet^r$ CFU | $Kan^r$ CFU total | $Kan^r$ CFU with inserts |
|---|---|---|---|---|
| 5,000 | 292 | 265 (100%) | 15 (5.7%) | 8 (3%) |

TABLE 7

Mycobacteriophage L5 DNA fragments introduced into pYUB763

| Clone | Kan | Number of inserted nucleotides | Number of inserted Sau3AI fragments | Orientation of insert | Sequence match to L5 genome: starts at bp | ends at bp | Name of corresponding gene | Total number of inserted amino acids | Number of stop codons | Frameshifts caused |
|---|---|---|---|---|---|---|---|---|---|---|
| pYUB763 | R | 6 | none | — | — | — | — | 2 | 0 | no |
| #4 | R | 156 | 1 | forward | 1,523 | 1,672 | gene 2 | 52 | 0 | no |
| #8 | R | 96 | 1 | forward | 33,496 | 33,408 | gene 50 | 32 | 0 | no |
| #10 | R | 135 | 4 | (1) reverse | 41,997 | 42,053 | gene 66 | 45 | 0 | no |
| | | | | (2) forward | 30,994 | 30,969 | gene 46 | | | |
| | | | | (3) forward | 39,898 | 39,879 | gene 61 | | | |
| | | | | (4) reverse | 5,348 | 5,274 | gene 10 | | | |

TABLE 7-continued Mycobacteriophage L5 DNA fragments introduced into pYUB763

| Clone | Kan | Number of inserted nucleotides | Number of inserted Sau3A1 fragments | Orientation of insert | Sequence match to L5 genome starts at bp | ends at bp | Name of corresponding gene | Total number of inserted amino acids | Number of stop codons | Frameshifts caused |
|---|---|---|---|---|---|---|---|---|---|---|
| #11 | R | 186 | 1 | forward | 15,830 | 15,646 | gene 25 | 62 | 0 | no |
| #12 | R | 30 | 1 | reverse | 22,987 | 22,964 | gene 31 | 10 | 0 | no |
| #15 | R | 75 | 1 | reverse | 17,872 | 17,805 | gene 26 | 25 | 0 | no |
| #16 | R | 48 | 1 | forward | 39,099 | 39,059 | gene 59 | 16 | 0 | no |
| #17 | R | 126 | 2 | (1) reverse | 5,529 | 5,459 | gene 11 | 42 | 0 | no |
|  |  |  |  | (2) reverse | 29,886 | 29,945 | gene 44 |  |  |  |
| #1 | S | 293 | 2 | (1) forward | 6,818 | 6,945 | gene 19 | 97.6 | 6 | yes |
|  |  |  |  | (2) reverse | 26,358 | 26,516 | gene 35 |  |  |  |
| #2 | S | 532 | 4 | (1) reverse | 40,774 | 40,804 | gene 65 | 177.3 | 3 | yes |
|  |  |  |  | (2) reverse | 8,468 | 8,437 | gene 14 |  |  |  |
|  |  |  |  | (3) forward | 37,476 | 37,351 | gene 55 |  |  |  |
|  |  |  |  | (4) forward | 14,218 | 14,522 | gene 23 |  |  |  |
| #5 | S | 504 | 3 | (1) forward | 30,671 | 30,607 | gene 45 | 168 | 2 | no |
|  |  |  |  | (2) reverse | 12,633 | 12,472 | gene 19 |  |  |  |
| #20 | S | 135 | 2 | (3) reverse | 22,963 | 22,693 | gene 31 |  |  |  |
|  |  |  |  | (1) forward | 40,582 | 40,508 | gene 64 | 45 | 3 | no |
| #28 | S | 87 | 1 | (2) forward | 12,675 | 12,723 | gene 19 |  |  |  |
|  |  |  |  | reverse | 13,862 | 13,882 | gene 22 | 29 | 1 | no |
| #30 | S | 67 | 3 | (1) reverse | 5,197 | 5,157 | gene 10 | 22.3 | 1 | yes |
|  |  |  |  | (2) reverse | 5,156 | 5,148 | gene 10 |  |  |  |
| #31 | S | 30 | 1 | (3) forward | 12,663 | 12,674 | gene 19 |  |  |  |
|  |  |  |  | forward | 20,108 | 20,131 | gene 28 | 10 | 1 | no |
| #34 | S | 73 | 1 | forward | 44,002 | 43,938 | gene 67 | 24.3 | 1 | yes |
| #39 | S | 225 | 3 | (1) forward | 36,612 | 36,521 | gene 54 | 75 | 4 | no |
|  |  |  |  | (2) forward | 18,256 | 18,334 | gene 26 + 27 |  |  |  |
|  |  |  |  | (3) reverse | 5,243 | 5,197 | gene 10 |  |  |  |
| #40 | S | 72 | 2 | (1) forward | 44,474 | 44,510 | beta-lactamase[1] | 24 | 1 | no |
|  |  |  |  | (2) reverse | 15,925 | 15,896 | gene 26 |  |  |  |

[1]matching to the DNA sequence of phAE41

TABLE 8

Protein splicing efficiency of plasmid pYUB763 with inserted mycobacteriophage L5 DNA fragments in *E.coli*

| Plasmid | Experiment | Tet$^r$ CFU[1] | Kan$^r$ CFU[2] | Frequency of Kan$^r$ CFU |
|---|---|---|---|---|
| #4 | 1 | 2.2 × 10$^9$/ml | 5.1 × 10$^6$/ml | 1/432 |
| #8 | 1 | 1.7 × 10$^9$/ml | 5.1 × 10$^6$/ml | 1/333 |
| #10 | 1 | 2.1 × 10$^9$/ml | 6.5 × 10$^6$/ml | 1/323 |
| #11 | 1 | 1.6 × 10$^9$/ml | 3.4 × 10$^4$/ml | 1/47,059 |
| #12 | 1 | 9.0 × 10$^8$/ml | 3.0 × 10$^6$/ml | 1/300 |
| #15 | 1 | 2.0 × 10$^9$/ml | 6.6 × 10$^6$/ml | 1/303 |
| #16 | 1 | 1.0 × 10$^9$/ml | 6.5 × 10$^6$/ml | 1/154 |
| #17 | 1 | 1.0 × 10$^9$/ml | 5.2 × 10$^6$/ml | 1/192 |

[1]incubation for 1 d at 37° C.
[2]incubation for 1 d at 37° C., plus 3 d at 30° C.

Figure 12:
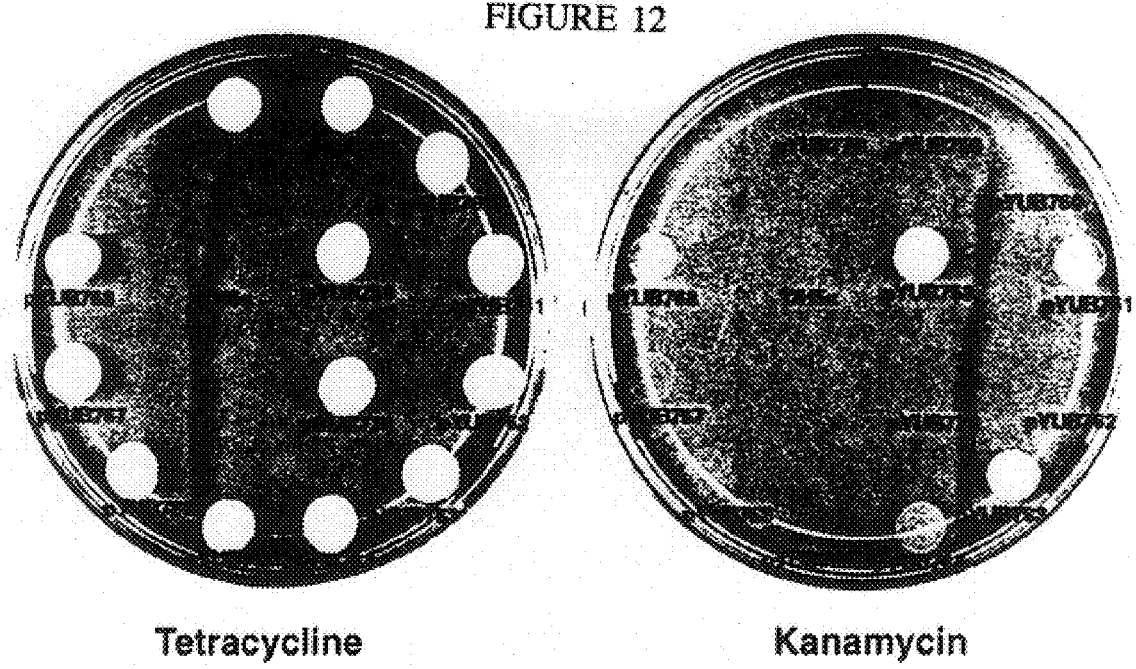
FIG. 12.

Additional Bgl II mutants of the *M. tuberculosis* recA intein. 8 additional constructs were generated which have Bgl II mutations spanning most of the intein sequence (see Table 9). All mutants were sequenced and submitted to double restriction digests with Bgl II and EcoRV to confirm the correctness of the Bgl II insertion. When analyzing protein splicing in these mutants, only 4 out of 11 clones were Kan$^r$, and of these, pYUB763 (with the Bgl II site inserted at 510 bp) was by far the best construct (see FIG. 12). This data supports the finding that this construct is best suited to be used for the selection and identification of open reading frames. pYUB763 was deposited in the American Type Culture Collection (ATCC), 12301 Parklawn Drive, Rockville, Md., 20852, on Mar. 11, 1997, under ATCC Accession Number __,__,__. This deposit was made pursuant to and in satisfaction of the Budapest Treaty on the International Recognition of the Deposit of Microorganisms for the Purposes of Patent Procedure.

TABLE 9

Primers Used to Generate Additional Bgl II Insertion Mutations in the *M. tuberculosis* recA Intein.

| Construct | Position of the Bgl II site | Primer | Sequence |  |
|---|---|---|---|---|
| pYUB760 | 204 bp | P29 | ggaagatctGCGACACCCGATCACAAGGTG[1] | (SEQ ID NO:48) |
|  |  | P30 | ggaagatctCCACACGATGGCGCCACCGGC | (SEQ ID NO:49) |
| pYUB761 | 306 bp | P31 | ggaagatctGTGACAGTGCGCCGATTCCG | (SEQ ID NO:50) |
|  |  | P32 | ggaagatctGAATCCATCGAAGCGTCGCGG | (SEQ ID NO:51) |

TABLE 9-continued

Primers Used to Generate Additional Bgl II
Insertion Mutations in the *M. tuberculosis* recA Intein.

| Construct | Position of the Bgl II site | Primer | Sequence | |
|---|---|---|---|---|
| pYUB762 | 408 bp | P33 | ggaagatctATCAATGTTCAGCGGGCGCTC | (SEQ ID NO:52) |
| | | P34 | ggaagatctGAAGTTGATCGGAGTCTTGCC | (SEQ ID NO:53) |
| pYUB765 | 714 bp | P43 | ttattattaagatctACGACCTCTGAACAACTC | (SEQ ID NO:54) |
| | | P44 | ttaattattaagatctCGTGTAACCGACCCGAAG | (SEQ ID NO:55) |
| pYUB766 | 816 bp | P45 | ttattattaagatctATCGTCAACGGTCGACGG | (SEQ ID NO:56) |
| | | P46 | ttattattaagatctGCTCGGCCGCTTCTGGGT | (SEQ ID NO:57) |
| pYUB767 | 918 bp | P49 | ggaagatctGGGCCGCGCGGTGCCGCGCTT | (SEQ ID NO:58) |
| | | P50 | ggaagatctCCACATGGGAACTGACTCCGC | (SEQ ID NO:59) |
| pYUB768 | 1020 bp | P51 | ggaagatctGTGCTGAATTATCTGGACGAG | (SEQ ID NO:60) |
| | | P52 | ggaagatctGGCATCGGTCATCTCTGCAGC | (SEQ ID NO:61) |
| pYUB770 | 1224 bp | P55 | ggaagatctATCCGAAGTGCTGCCAACG | (SEQ ID NO:62) |
| | | P56 | ggaagatctCACGGATAGCGGAGTTCTTC | (SEQ ID NO:63) |

[1]letters in lower case represent the Bgl II restriction site with several additional bp Generation of pYUB771, a plasmid carrying an in frame deletion of 102 base pairs within the *M. tuberculosis* recA intein. Experiments were performed to determine if an in frame deletion made between base pairs 510 and 612 within the *M. tuberculosis* recA intein would still be able to support protein splicing. When plasmid pYUB771 was generated by ligating double digests of pYUB763 and pYUB764 cut by Bgl II and Ast II, the resulting construct was found to be Kan$^s$ (Table 10). It could therefore be concluded that this region within the *M. tuberculosis* recA intein is essential and cannot be deleted.

TABLE 10

Phenotypes of various BgI II insertion mutants
in the *M. tuberculosis* recA intein:

| Plasmid name | Insertion point of the BgI II site | Kan resistance | Comments |
|---|---|---|---|
| pYUB763 | 510 bp | r | first ORFTRAP vector |
| pYUB771 | 510 bp | s | deletion of bp 510 to bp 612 |
| pYUB774 | 508 bp | s | second ORFTRAP vector (2 bp frameshift) |

A Library of *Haemophilus influenza* for the Isolation of Open Reading Frames. Because the entire chromosome of *H. influenza* has been sequenced (Fleischmann, R. D. et al., *Science*, 296:496–512 (1995)), an *H. influenza* system was used for the isolation of open reading frames as quality control. Using an *H. influenza* digest as donor DNA, it can be determined if the trapped inteins are randomly chosen from a chromosomal digest, or whether certain inteins are preferentially inserted. It may also be estimated how representative the library is, i.e. to show that any Sau3A1 fragment of the right reading frame would indeed be included in a library for the identification of inteins.

With the mycobacteriophage L5 library, the inventors have observed that multiple Sau3A1 fragments could ligate before being inserted into the plasmid used for isolating an intein, thus creating "synthetic" open reading frames. In order to prevent this process from happening with the *H. influenza* library, DNA fragments from a complete 24 hour digest were dephosphorylated with calf intestinal phosphatase (Boehringer Mannheim) before ligation to the vector DNA.

The inventors have also altered the pYUB763 vector by making a 2 bp deletion just before the Bgl II site of the *M. tuberculosis* recA intein at bp 510, thus creating plasmid pYUB774. The 2 bp deletion caused a frameshift and, as a consequence, four stop codons to occur within the intein sequence. As expected, *E. coli* transformed with pYUB774 were Kan$^r$ (Table 10, FIG. 12). The plasmid was sequenced to confirm correctness of the frameshift (data not shown). When used as a vector for trapping open reading frames, the reading frame of plasmid pYUB744 should be restored upon insertion of an open reading frame of the correct complementing reading frame, therefore rendering transformed bacteria to be Kan$^r$. Using pYUB774 as the new vector for trapping open reading frames, the inventors hope to be able to reduce the background (consisting mainly of bacteria transformed with "empty" vector plasmids) to almost null, so that basically any Kan$^r$ colony that appears after ligation of the vector to the *H. influenza* fragments contains an inserted open reading frame. Data obtained from the first *H. influenza* clones confirmed the hypothesis that every clone that contained an open reading frame of the n+2 reading frame was able to restore Kan$^r$ resistance (data not shown). The largest open reading frame sequenced thus far has a length of 251 bp (data not shown). This fact demonstrates that the largest insert (180 bp) in the mycobacteriophage L5 trap for open reading frames was in fact not the maximum size of an insert to be tolerated by the *M. tuberculosis* recA intein.

C. Discussion

In this study, the design of vector constructs is described for use as a novel tool for the identification of translated open reading frames from genomic libraries, by exploiting the unique protein splicing properties of the *M. tuberculosis* recA intein. While genomic libraries have been used before to search for a pathogen's protective antigens, this endeavor was difficult because of the large number of constructs that had to be screened because there was no selection system which identified well expressed open reading frames while discriminating against those fragments that contained non coding DNA sequences or stop codons. However, if one could select translated open reading frames from a genomic library, time and cost of such an investigation could be cut down significantly. The goal was to find a suitable region within the *M. tuberculosis* recA intein that would tolerate the insertion of additional genetic material while still allowing the intein to splice. In order to develop the vector constructs, the *M. tuberculosis* recA intein was cloned into the kanamycin resistance gene aph, so that successful protein splicing events would be reported by transformed bacteria (*E.*

*coli* and mycobacteria) growing on media containing Kan. It has been shown by a number of investigators that inteins can be moved into a different host gene context without affecting protein splicing, consequently host genes play only a minor role (Davis and Colston, *Cell*, 71:201–210 (1992); Cooper, et al., *EMBO Journal*, 12:2575–2583 (1993)). For instance, the *M. tuberculosis* recA has been cloned into the alpha-fragment of beta-galactosidase (Davis, et al., *Cell*, 71:201–210 (1992)), and the *S. cerevisiae* VMA1 intein has been cloned into the VAT2 gene, which is a selectable marker, as it can complement an auxotrophic yeast strain (Cooper, et al., *EMBO Journal*, 12:2575–2583 (1993)). The Pyrococcus sp. GB-D DNA polymerase intein has been cloned into a synthetic chimeric gene with a maltose binding protein at the N-terminal side of the intein, and paramyosin ΔSal at the C-terminal side of the intein (Xu, et al., *Cell*, 75:1371–1377 (1993)). A brand-new application is a protein purification system which uses this intein to overexpress toxic proteins in *E. coli* by creating an intein containing fusion protein, purifying it by affinity chromatography and using conditional protein splicing to remove the intein from the precursor ("Impact", NEB). In all cases, inteins can splice out of their host proteins, provided that the hexapeptides at the splice sides are not disturbed. For development of the vector constructs of the present invention, a selectable rather than a screenable marker was needed since whole genomic libraries were to be cloned into the *M. tuberculosis* recA intein, and the events for which this system was designed to detect are rare. After all, only one out of three reading frames will be tolerated, and most likely in only one orientation. Five out of six fragments will therefore not be tolerated, but because of a selectable system, these clones will not even be visible, making it easy to screen for the successfully trapped inserts.

Insertion of DNA sequences into the *M. tuberculosis* recA intein proved to be difficult, since basically nothing is known about its protein structure. Extensive deletion analysis showed that while the *M. tuberculosis* recA intein tolerated a small 99 bp in frame deletion in its center, most of the larger deletions inhibited splicing (Davis et al., *Cell*, 71:201–210 (1992)). It was therefore assumed that the central region of the intein might be a non essential region and probably part of a loop structure. This supposition was supported by studies done in the *S. cerevisiae* VM1 intein, where the investigators showed that small deletions in the central were acceptable, but furthermore, an insertion of 7 amino acids residues was also tolerated (Cooper, et al., *EMBO Journal*, 12:2575–2583 (1993)). The first attempt to insert foreign DNA fragments from a mycobacteriophage L5 HpaII digest into the *M. tuberculosis* recA intein was done using the unique AsuII site, which is located at 7,455 bp in plasmid pYUB750 (FIG. 1). However, although this site is very close to the C-terminal end of the 99 bp deletion that Davis, et al., *Cell*, 71:201–210 (1992) made, no truly $Kan^r$ clones with inserted mycobacteriophage L5 sequences were found (data not shown). After that first erratic approach, it was decided to use a more systematic procedure, employing a linker scanning analysis. By employing LR-PCR, a unique Bgl II restriction site was inserted into three different positions of the *M. tuberculosis* recA intein. A Bgl II restriction site has 6 bp, which encode for an arginine and a serine residue. It could be shown that inserting as little as these two amino acids into the intein was deleterious to protein splicing in plasmid pYUB759 (at amino acid position 34), whereas it was well tolerated in plasmid pYUB763 (at amino acid position 170). When the location of the Bgl II site in pYUB763 was compared with the published data about deletions and insertion in inteins, a common feature became apparent: all tolerated deletions and insertions including those of the inventors were made in the central part of the inteins, between the conserved dodecapeptide motifs P1 and P2 (Pietrokowski, *Protein Science*, 3:2340–2350 (1994)). Although it is only speculative, this could mean that all inteins share a conserved loop structure in this area. Insertion of a Bgl II site at position 612 bp of the *M. tuberculosis* recA intein (plasmid pYUB764, at amino acid position 204) was tolerated to some extent, but protein splicing was definitely impaired. Even though position 612 bp was not useful to insert a genomic library, a large in frame deletion will be created between 510 bp and 612 bp in the *M. tuberculosis* recA intein by cleaving plasmids pYUB763 and pYUB764 with Bgl II and then fusing the fragments. Since plasmid pYUB763 fully allowed protein splicing, and plasmid pYUB764 facilitated splicing at least partially, it is contemplated that this new construct will still splice and allow for insertion of larger pieces of foreign DNA. Using LR-PCR, the inventors had the means to analyze the protein structure of the intein by inserting a new Bgl II site in any part of the *M. tuberculosis* recA intein. Eventually, 12 different constructs will be generated with two extra amino acids inserted in increments of 102 bp, thus interrupting the intein once between each 34 amino acid residues. Thus, it would then be possible to roughly map the essential and non essential regions of the *M. tuberculosis* recA intein. The usefulness for a vector construct of plasmid pYUB763 with a Bgl II insertion at 510 bp of the *M. tuberculosis* recA intein was analyzed by introducing an additional small open reading frame. The influenza virus hemagglutinin (HA) epitope which was chosen for this task is only 9 amino acids long, and with the amino acids encoded by the restriction sites, a total number of 13 amino acid residues would be introduced into the intein (FIG. 7). The HA tag is a commonly used molecular marker, and a commercially available monoclonal antibody, 12CA5, enabled the inventors to identify two recombinant clones with the tag inserted in forward orientation. It could then be shown that the HA epitope was well tolerated in plasmid pYUB763, and that it did not impair protein splicing at all. Furthermore, the HA tag allowed for identification of the intein containing precursor proteins as well as different splice forms in a Western blot (FIG. **9*b***). Inteins appear to be stable structures once they are spliced out of their precursor proteins, so HA tags may be a useful way to purify these molecules by affinity chromatography or using magnetic beads. The insertion of an HA epitope (13 amino acids) into the *M. tuberculosis* recA intein was the largest piece of DNA introduced into an intein to date (6 amino acids larger than the 7 amino acid insertion published by Cooper, et al., *EMBO Journal*, 12:2575–2583 (1993)).

The first successful vector construct experiment was done using plasmid pYUB763 and cloning a Sau3AI digest of mycobacteriophage L5 DNA (which was prepared from a shuttle phasmid, phAE41) into the Bgl II site. From the 292 clones that were plated on Tet containing media, 15 proved to be truly $Kan^r$, and 8 of these had inserts. These 8 clones represented 3% of the plated clones, thus confirmed the initial assumption that the events to be detected are rare. However, supported by our selectable marker system, these 8 clones were easily identified. Sequence analysis verified that the "trapped" inserts in these 8 clones were in fact open reading frames, and all 8 could be matched to mycobacteriophage L5 genes (Table 7). However, only four out of eight L5 fragments were inserted in forward orientation, two were inserted reverse and two were concatamers of multiple Sau3AI fragments in various orientations. This result demonstrates the power of the vector constructs of the present invention to select for open reading frames. To ensure that only forward oriented open reading frames get expressed, a refined vector which can hold larger DNA fragments can be utilized. An intended pYUB763/pYUB764 fusion plasmid carrying a deletion of 102 bp in *M. tuberculosis* recA intein may be sufficient to hold larger inserts. In addition, the vector may be altered so that inserts can be trapped in all three reading frames by inserting one or two extra bp before the cloning site. A set of these three vector constructs could then be used to create a genomic library, thus ensuring that three out of six fragments can get expressed.

All inserts from ten Kan$^s$ control clones were non open reading frames showing between one to six stop codons as well as a number of frame shifts. All of the ten inserts could be matched to mycobacteriophage L5 or phAE41 genes, and not a single insert represented a part of the non coding regions of the L5 genome. However, this may be due to the fact that L5 has a high gene density and has only few non coding DNA sequences (Hatful and Sarkis, *Mol. Microbiol.*, 7:395–405 (1993)). Another organism but a virus may be more appropriate to assess the power of the vector constructs of the present invention to discriminate between open reading frames and non open reading frames in a genome, but the overall principle of this system could be demonstrated here. The largest insert consisted of 62 amino acids and still allowed protein splicing to occur, although the splice frequency was somewhat reduced (Table 8). However, the second largest insert (52 amino acids) allowed splicing to occur at the same frequency than a 10 amino acid insert, so either the critical insert size has been reached with introducing 62 amino acids, or some other problem is responsible for this behavior. The latter hypothesis is supported by a different splice pattern of the respective clone #11 in a minicell analysis, showing an additional band around 50 kDa (FIG. 10). One interesting feature of this experiment was that a number of inserts consisted of multiple Sau3AI fragments which had been formed before inserting into the Bgl II site. As long as the reading frame was not changed and no stop codons appeared, this did not affect protein splicing. While "fragment shuffling" may not be desirable in protective antigen studies, this easy way of epitope mixing may be of interest in other cases. If it has to be prevented, the inserts could be dephosphorylated and cloned into a non-dephosphorylated vector.

There are many ways in which the vector constructs of the present invention could be useful. The concept of DNA vaccination is perhaps the most appealing application. If a genomic library from a pathogen could be cloned into a vector construct of the present invention, and the enriched library could be directly injected into an animal, one could know in very short time if any of the open reading frames that are represented in the library encode for protective antigens. In order to identify individual protective open reading frames, the library would have to be broken down into pools and injected into several animals. However, knowledge about the presence or absence of protective antigens in a reasonable time would not only be very encouraging to the researcher, but also be extremely helpful when one is working with slow growing organisms, like *M. tuberculosis* or *M. bovis* BCG. The plasmid pYUB763 will be further developed to make it useful for DNA vaccination, which would first of all require the identification of a useful promoter that would ideally work both in *E. coli* and in eukaryotic cells to drive expression of the aph'-intein-aph' precursor.

A genomic library employing the vector constructs of the present invention could be useful when (i) many antigens have already been identified as well as when (ii) basically nothing is known about the protective antigens of an organisms, but protective immunity has been observed. In the first case, the library would be helpful to find out if some antigens have been missed, especially if they are only expressed in vivo, or when most knowledge has been derived from studies with cDNA (because its complexity depends on culture conditions). In the case of an organism where very little is known about individual protective antigens, sequencing of the trapped open reading frames and aligning those sequences to databases would give a first impression of the nature of the antigens. If the individual protective open reading frames have to be identified, the vector constructs containing open reading frames may be transformed into *M. bovis* BCG organisms. As recombinant *M. bovis* BCG has been shown before to stimulate protective immune responses to a variety of antigens, and is also known to keep extrachromosomal plasmids for several months in vivo, it seems to be a suitable vector to express trapped open reading frames in animal models (Stover et al., *Nature*, 351:456–460 (1991)). The vector construct library of the present invention would have to be pooled and injected into small groups of animals. After challenge with the relevant pathogen, surviving animals are expected to harbor recombinant *M. bovis* BCG expressing the protective open reading frames. Sacrificing those animals and cultivating *M. bovis* BCG from spleens and livers would yield most of the clones expressing protective open reading frames. By sequencing the inserts, the identity or diversity of the inserted open reading frames could be determined, and if necessary, a second round of protection and challenge experiments can be performed. The vector pYUB763 is not suitable for expression in *M. bovis* BCG as it is, because the mycobacterial origin of replication oriM has been partially deleted. However, by using PCR, the missing part can easily be amplified and oriM can be restored by a simple cloning step. Also, the second antibiotic marker which confers resistance to tetracycline would have to be exchanged for a hygromycin marker, because tetracycline is not very stable and breaks down during the three weeks culture time that *M. bovis* BCG requires.

Yet another application of the vector constructs of the present invention would be to use them as an "epitope-trap", i.e. for the isolation and identification of epitopes. The vector constructs may be used to generate genomic libraries of expressed epitopes from any pathogen in any recombinant vaccine vector system including, but not limited to, recombinant BCG, DNA vaccine vectors, vaccinia virus, fowl pox virus, recombinant Shigella, recombinant Salmonella, pseudorabies virus, recombinant Streptococci, and any recombinant mycobacterial vaccine vector. A number of protective antigens have been characterized at the immunological level, but no knowledge exists about the protein epitopes that are responsible for protectivity. The usual way to tackle this problem would be to use a library of overlapping peptides and characterize them with a specific T-cell line or clone. B-cell epitopes are harder to identify because they are often conformational epitopes, thus requiring a three dimensional structure. An alternative in T-cell research is to elute the MHC bound material by treatment with acid, followed by separation of the peptides and individual testing with specific T-cell lines or clones. However, if the gene encoding for this particular protein has been cloned, it could be digested into rather small fragments and inserted into a vector construct of the present invention. T-cell epitopes are usually between 9 and 15 amino acids in length, which is completely compatible with the insert size that has been identified so far (from 2 to 62 amino acids). As all T-cell epitopes have to be processed within an antigen presenting cell, the only concern is whether the *M. tuberculosis* recA intein would be cleaved correctly by the proteasome. If a certain amino acid configuration has to be present around the insertion site of the library, these residues may have to be added to ensure maximum processing of foreign epitopes. Protective epitopes expressed in the vector constructs of the present invention could be screened either in proliferation tests and/or cytokine assays using recombinant *E. coli* or *M. bovis* BCG as antigens and specific T cells as effector cells. If screening by cytotoxic T cells is desirable, one has to find a way to target recombinant inteins into the cytoplasm of the antigen presenting cells to ensure that the antigenic epitopes are presented in context with MHC class I molecules. Recently, an auxotrophic *Shigella flexneri* strain that carries a deletion in the asd gene has been described (Sizemore, et al., *Science*, 270:299–302 (1995)). This mutant Shigella strain cannot synthesize diaminopimelic acid, therefore its cell walls are extremely weak, so that bacteria die after a couple of replication cycles (Sizemore, et al., *Science*, 270:299–302 (1995)). These Shigella mutants have been successfully used to deliver plasmid DNA to mucosal cells, where they die soon, but they can still target recombinant antigens into the host cell cytoplasm. Consequently, a mutant strain like this would be a good vector to deliver open reading frames inserted in to an intein into antigen presenting cells, and since *E. coli* plasmids replicate well in Shigella strains, it would be easy to accomplish this strategy using the pYUB763 vector.

The vector constructs of the present invention may also be used for the generation of a genomic library of expressed epitopes in-frame with a defined epitope to link an epitope from any pathogen (such as HIV) to identify an epitope that can mediate a specific immunological response. The vector constructs may also be used to generate gene libraries of expressed epitopes from any specific gene in any recombinant vaccine vector including, but not limited to, recombinant BCG, DNA vaccine vectors, vaccinia virus, fowl pox virus, recombinant Shigella, recombinant Salmonella, pseudorabies virus, recombinant Streptococci, and any recombinant mycobacterial vaccine vector. A further use of the vector constructs of the present invention is in the optimization of protein expression of any DNA fragment encoding any open reading frame. The vector constructs of the present invention may also be used to generate novel enzyme activities by linking a defmed protein domain of a specific function with a library of domains of other functions.

What is claimed is:

1. A vector construct comprising:

(a) an origin of replication;

(b) a DNA sequence encoding a selectable marker;

(c) a DNA sequence encoding an intein, said DNA sequence having a unique restriction enzyme site;

(d) a DNA sequence encoding critical amino acid residues located at the splice junctions of said DNA sequence encoding said intein; and (e) a DNA sequence encoding regulatory elements so as to effect expression of the vector construct in a host cell.

2. The vector construct of claim 1 wherein the DNA sequence encoding an intein is obtained from procaryotic or eucaryotic DNA.

3. The vector construct of claim 2 wherein the procaryotic DNA having a sequence encoding an intein is obtained from bacteria.

4. The vector construct of claim 3 wherein the bacteria is eubacteria or archaebacteria.

5. The vector construct of claim 4 wherein the eubacteria is Mycobacteria.

6. The vector construct of claim 4 wherein the archaebacteria is Pyrococcus, Thermococcus, or Methanococcus.

7. The vector construct of claim 5 wherein the mycobacterial DNA has a sequence encoding RecA intein.

8. The vector construct of claim 7 wherein the mycobacterial DNA having a sequence encoding the RecA intein is obtained from a mycobacterium selected from the group consisting of *Mycobacterium bovis* BCG, *Mycobacterium leprae, Mycobacterium microti*, and *Mycobacterium tuberculosis.*

9. The vector construct of claim 6 wherein the pyrococcal DNA encodes Psp pol intein.

10. The vector construct of claim 6 wherein the thermococcal DNA encodes Tli pol intein-1 or Tli pol intein-2.

11. The vector construct of claim 7 wherein the DNA sequence encoding the mycobacterial RecA intein contains a restriction site.

12. The vector construct of claim 11 wherein the restriction site is a BglII restriction site.

13. The vector construct of claim 2 wherein the eucaryotic DNA encoding an intein is obtained from yeast.

14. The vector construct of claim 13 wherein the yeast DNA encoding an intein is obtained from *Saccharomyces cerevisiae* or *Candida tropicalis.*

15. The vector construct of claim 14 wherein the *Saccharomyces cerevisiae* DNA encodes Sce VMA intein.

16. The vector construct of claim 1 wherein the DNA sequence encoding the critical amino acid residues located at the splice junctions of the intein encode for the amino acids selected from the group consisting of histidine, asparagine, cysteine, threonine, and serine.

17. The vector construct of claim 7 wherein the mycobacterial RecA intein contains an N'-terminal cysteine residue and a C'-terminal cysteine residue.

18. The vector construct of claim 1 wherein the DNA sequence encoding the selectable marker is selected from the group consisting of herpes simplex virus DNA, vaccinia virus thymidine kinase DNA, adenine phosphoribosyltransferase DNA, hypoxanthine-guanine phosphoribosyltransferase DNA, aspartate transcarbamylase DNA, ornithine decarboxylase DNA, aminoglycoside phosphotransferase DNA, hygromycin-B-phosphotransferase (aph) DNA, xanthine-guanine phosphoribosyltransferase DNA, tryptophan synthetase DNA, histidinol dehydrogenase DNA, multiple drug resistance DNA, dihydrofolate reductase DNA, carbamyl phosphate synthetase, aspartate transcarbamylase, and dihydroorotase (CAD) DNA, adenosine deaminase DNA, asparagine synthetase DNA, and glutamine synthetase DNA.

19. The vector construct of claim 18 wherein the aph selectable marker gene confers resistance to kanamycin.

20. The vector construct of claim 1 comprising an additional selectable marker gene.

21. The vector construct of claim 20 wherein the additional selectable marker gene is selected from the group consisting of the chloramphenicol resistance gene, tetracycline resistance gene, hygromycin resistance gene, geneticin resistance gene, B-galactosidase gene, ampicillin resistance gene, herpes simplex virus gene, vaccinia virus thymidine kinase gene, adenine phosphoribosyltransferase gene, hypoxanthine-guanine phosphoribosyltransferase gene, aspartate transcarbamylase gene, ornithine decarboxylase gene, aminoglycoside phosphotransferase gene, hygromycin-B-phosphotransferase gene, xanthine-guanine phosphoribosyltransferase gene, tryptophan synthetase gene, histidinol dehydrogenase gene, multiple drug resistance gene, dihydrofolate reductase gene, carbamyl phosphate synthetase, aspartate transcarbamylase, and dihydroorotase (CAD) gene, adenosine deaminase gene, asparagine synthetase gene, and glutamine synthetase gene.

22. A vector construct comprising:
(a) an origin of replication;
(b) a DNA sequence encoding a selectable marker;
(c) a DNA sequence encoding an intein, said DNA sequence having a unique restriction enzyme site;
(d) a DNA sequence encoding critical amino acid residues located at the splice junctions of said intein;
(e) a DNA sequence encoding regulatory elements so as to effect expression of the vector construct in a host cell; and
(f) a DNA of interest inserted into the unique restriction site of the intein.

23. The vector construct of claim 22 wherein the DNA sequence encoding an intein is obtained from procaryotic or eucaryotic DNA.

24. The vector construct of claim 23 wherein the procaryotic DNA having a sequence encoding an intein is obtained from bacteria.

25. The vector construct of claim 24 wherein the bacteria is eubacteria or archaebacteria.

26. The vector construct of claim 25 wherein the eubacteria is Mycobacteria.

27. The vector construct of claim 25 wherein the archaebacteria is Pyrococcus, Thermococcus, or Methanococcus.

28. The vector construct of claim 26 wherein the mycobacterial DNA has a sequence encoding RecA intein.

29. The vector construct of claim 28 wherein the mycobacterial DNA having a sequence encoding the RecA intein is obtained from a mycobacterium selected from the group consisting of *Mycobacterium bovis* BCG, *Mycobacterium leprae*, *Mycobacterium microti*, and *Mycobacterium tuberculosis*.

30. The vector construct of claim 27 wherein the pyrococcal DNA encodes Psp pol intein.

31. The vector construct of claim 27 wherein the thermococcal DNA encodes Tli pol intein-1 or Tli pol intein-2.

32. The vector construct of claim 28 wherein the DNA sequence encoding the mycobacterial RecA intein contains a restriction site.

33. The vector construct of claim 32 wherein the restriction site is a BglII restriction site.

34. The vector construct of claim 23 wherein the eucaryotic DNA encoding an intein is obtained from yeast.

35. The vector construct of claim 34 wherein the yeast DNA encoding an intein is obtained from *Saccharomyces cerevisiae* or *Candida tropicalis*.

36. The vector construct of claim 35 wherein the *Saccharomyces cerevisiae* DNA encodes Sce VMA intein.

37. The vector construct of claim 22 wherein the DNA sequence encoding the critical amino acid residues located at the splice junctions of the intein encode for the amino acids selected from the group consisting of histidine, asparagine, cysteine, threonine, and serine.

38. The vector construct of claim 28 wherein the mycobacterial RecA intein contains an N'-terminal cysteine residue and a C'-terminal cysteine residue.

39. The vector construct of claim 22 wherein the DNA sequence encoding the selectable marker is selected from the group consisting of herpes simplex virus DNA, vaccinia virus thymidine kinase DNA, adenine phosphoribosyltransferase DNA, hypoxanthine-guanine phosphoribosyltransferase DNA, aspartate transcarbamylase DNA, ornithine decarboxylase DNA, aminoglycoside phosphotransferase DNA, hygromycin-B-phosphotransferase (aph) DNA, xanthine-guanine phosphoribosyltransferase DNA, tryptophan synthetase DNA, histidinol dehydrogenase DNA, multiple drug resistance DNA, dihydrofolate reductase DNA, carbamyl phosphate synthetase, aspartate transcarbamylase, and dihydroorotase (CAD) DNA, adenosine deaminase DNA, asparagine synthetase DNA, and glutamine synthetase DNA.

40. The vector construct of claim 39 wherein the aph selectable marker gene confers resistance to kanamycin.

41. The vector construct of claim 22 comprising an additional selectable marker gene.

42. The vector construct of claim 41 wherein the additional selectable marker gene is selected from the group consisting of the chloramphenicol resistance gene, tetracycline resistance gene, hygromycin resistance gene, geneticin resistance gene, B-galactosidase gene, ampicillin resistance gene, herpes simplex virus gene, vaccinia virus thymidine kinase gene, adenine phosphoribosyltransferase gene, hypoxanthine-guanine phosphoribosyltransferase gene, aspartate transcarbamylase gene, ornithine decarboxylase gene, aminoglycoside phosphotransferase gene, hygromycin-B-phosphotransferase gene, xanthine-guanine phosphoribosyltransferase gene, tryptophan synthetase gene, histidinol dehydrogenase gene, multiple drug resistance gene, dihydrofolate reductase gene, carbamyl phosphate synthetase, aspartate transcarbamylase, and dihydroorotase (CAD) gene, adenosine deaminase gene, asparagine synthetase gene, and glutamine synthetase gene.

43. The vector construct of claim 22 wherein the DNA of interest is an open reading frame DNA sequence.

44. The vector construct of claim 43 wherein the open reading frame DNA sequence encodes all or a portion of a DNA sequence encoding a protein or polypeptide.

45. The vector construct of claim 44 wherein the DNA sequence encoding a protein or polypeptide is an antigen.

46. The vector construct of claim 45 wherein the antigen is selected from the group consisting of *Mycobacterium leprae* antigens, *Mycobacterium tuberculosis* antigens, *Mycoplasma pulmonis* antigens, *Mycobacterium bovis* BCG antigens, Rickettsia antigens, malaria sporozoites and merozoites, diptheria toxoids, tetanus toxoids, Clostridium antigens, Leishmania antigens, Salmonella antigens, Borrelia antigens, *Mycobacterium africanum* antigens, *Mycobacterium avium* antigens, *Mycobacterium intracellulare* antigens, Treponema antigens, Pertussis antigens, Schistosoma antigens, Filaria antigens, Herpes virus antigens, Shigella antigens, Neiserria antigens,mycobacteriophage L5 antigens, *Haemophilus influenzae* antigens, rabies antigens, pseudorabies virus antigens, polio virus antigens, Rift Valley Fever virus antigens, dengue virus antigens, human immunodeficiency virus antigens, respiratory syncytial virus antigens, snake venom antigens, and Vibrio cholera antigens.

47. The vector construct of claim 45 wherein the antigen is selected from a genomic library.

48. A method of determining if a DNA of interest is an open reading frame sequence comprising the steps of:
(a) obtaining a vector construct comprising an origin of replication; a DNA sequence encoding a selectable marker; a DNA sequence encoding an intein, said DNA sequence having a unique restriction enzyme site; a DNA sequence encoding critical amino acid residues located at the splice junctions of said intein; and a DNA sequence encoding regulatory elements so as to effect expression of the vector construct in a host cell;

(b) inserting said DNA of interest into the unique restriction site of the intein of said vector construct;

(c) introducing said vector construct into a host cell;

(d) growing the host cell;

(e) treating the host cell with a drug for the selective survival of the host cell; and (f) selecting the host cell exhibiting resistance to the drug thereby determining that a DNA of interest is an open reading frame sequence.

49. The method of claim 48 wherein the DNA sequence encoding an intein is obtained from procaryotic or eucaryotic DNA.

50. The method of claim 49 wherein the procaryotic DNA having a sequence encoding an intein is obtained from bacteria.

51. The method of claim 50 wherein the bacteria is eubacteria or archaebacteria.

52. The method of claim 51 wherein the eubacteria is Mycobacteria.

53. The method of claim 51 wherein the archaebacteria is Pyrococcus, Thennococcus, or Methanococcus.

54. The method of claim 52 wherein the mycobacterial DNA has a sequence encoding RecA intein.

55. The method of claim 54 wherein the mycobacterial DNA having a sequence encoding the RecA intein is obtained from a mycobacterium selected from the group consisting of *Mycobacterium bovis* BCG, *Mycobacterium leprae*, *Mycobacterium microti*, and *Mycobacterium tuberculosis*.

56. The method of claim 53 wherein the pyrococcal DNA encodes Psp pol intein.

57. The method of claim 53 wherein the thermococcal DNA encodes Tli pol intein-1 or Tli pol intein-2.

58. The method of claim 54 wherein the DNA sequence encoding the mycobacterial RecA intein contains a restriction site.

59. The method of claim 58 wherein the restriction site is a BglII restriction site.

60. The method of claim 49 wherein the eucaryotic DNA encoding an intein is obtained from yeast.

61. The method of claim 60 wherein the yeast DNA encoding an intein is obtained from *Saccharomyces cerevisiae* or *Candida tropicalis*.

62. The method of claim 61 wherein the *Saccharomyces cerevisiae* DNA encodes Sce VMA intein.

63. The method of claim 48 wherein the DNA sequence encoding the critical amino acid residues located at the splice junctions of the intein encode for the amino acids selected from the group consisting of histidine, asparagine, cysteine, threonine, and serine.

64. The method of claim 54 wherein the mycobacterial RecA intein contains an N'-terminal cysteine residue and a C'-terminal cysteine residue.

65. The method of claim 48 wherein the DNA sequence encoding the selectable marker is selected from the group consisting of herpes simplex virus DNA, vaccinia virus thymidine kinase DNA, adenine phosphoribosyltransferase DNA, hypoxanthine-guanine phosphoribosyltransferase DNA, aspartate transcarbamylase DNA, ornithine decarboxylase DNA, aminoglycoside phosphotransferase (aph) DNA, hygromycin-B-phosphotransferase DNA, xanthine-guanine phosphoribosyltransferase DNA, tryptophan synthetase DNA, histidinol dehydrogenase DNA, multiple drug resistance DNA, dihydrofolate reductase DNA, carbamyl phosphate synthetase, aspartate transcarbamylase, and dihydroorotase (CAD) DNA, adenosine deaminase DNA, asparagine synthetase DNA, and glutamine synthetase DNA.

66. The method of claim 65 wherein the aph selectable marker gene confers resistance to kanamycin.

67. The method of claim 48 comprising an additional selectable marker gene.

68. The method of claim 67 wherein the additional selectable marker gene is selected from the group consisting of the chloramphenicol resistance gene, tetracycline resistance gene, hygromycin resistance gene, geneticin resistance gene, B-galactosidase gene, ampicillin resistance gene, herpes simplex virus gene, vaccinia virus thymidine kinase gene, adenine phosphoribosyltransferase gene, hypoxanthine-guanine phosphoribosyltransferase gene, aspartate transcarbamylase gene, ornithine decarboxylase gene, aminoglycoside phosphotransferase gene, hygromycin-B-phosphotransferase gene, xanthine-guanine phosphoribosyltransferase gene, tryptophan synthetase gene, histidinol dehydrogenase gene, multiple drug resistance gene, dihydrofolate reductase gene, carbamyl phosphate synthetase, aspartate transcarbamylase, and dihydroorotase (CAD) gene, adenosine deaminase gene, asparagine synthetase gene, and glutamine synthetase gene.

69. The method of claim 48 wherein the DNA of interest is any coding or non-coding DNA sequence.

70. The method of claim 69 wherein the coding or non-coding DNA sequence is an open reading frame DNA sequence.

71. The method of claim 70 wherein the open reading frame DNA sequence encodes all or a portion of a DNA sequence encoding a protein or polypeptide.

72. The method of claim 71 wherein the DNA sequence encoding a protein or polypeptide is an antigen.

73. The method of claim 72 wherein the antigen is selected from the group consisting of *Mycobacterium leprae* antigens, *Mycobacterium tuberculosis* antigens, *Mycoplasma pulmonis* antigens, *Mycobacterium bovis* BCG antigens, Rickettsia antigens, malaria sporozoites and merozoites, diptheria toxoids, tetanus toxoids, Clostridium antigens, Leishmania antigens, Salmonella antigens, Borrelia antigens, *Mycobacterium africanum* antigens, *Mycobacterium avium* antigens, *Mycobacterium intracellulare* antigens, Treponema antigens, Pertussis antigens, Schistosoma antigens, Filaria antigens, Herpes virus antigens, Shigella antigens, Neiserria antigens, rabies antigens, polio virus antigens, Rift Valley Fever virus antigens, dengue virus antigens, human immunodeficiency virus antigens, respiratory syncytial virus antigens, snake venom antigens, and Vibrio cholera antigens.

74. The method of claim 72 wherein the antigen is selected from a genomic library.

75. The method of claim 48 wherein the host cell is selected from the group consisting of *Escherichia coli, Salmonella typhimurium, Salmonella enteridis, Shigella dysenteriae, Shigella flexneri, Shigella sonnei, Mycobacterium bovis*-BCG, *Mycobacterium tuberculosis, Mycobacterium avium, Mycobacterium phlei, Mycobacterium intracellulare, Pichia pastoris, Chlamydomonas reinhardtii, Cryptococcus neoformans, Neurospora crassa, Podospora anserina, Saccharomyces cerevisiae, Saccharomyces pombe, Uncinula necator*, cultured insect cells, cultured chicken fibroblasts, cultured hamster cells, cultured human cells, and cultured mouse cells.

76. The method of claim 48 wherein the vector is introduced into the host cell using a method selected from the group consisting of electroporation, calcium chloride treatment, DEAE dextran, cationic liposome fusion, protoplast fusion, DNA coated-microprojectile bombardment, and infection with recombinant replication-defective retroviruses.

77. The method of claim 48 wherein the drug for the selective survival of the host cell is kanamycin, tetracycline, gentamycin, chloramphenicol, or ampicillin.

* * * * *

UNITED STATES PATENT AND TRADEMARK OFFICE
CERTIFICATE OF CORRECTION

Page 1 of 1

PATENT NO.       : 5,981,182
APPLICATION NO.  : 08/816721
DATED            : November 9, 1999
INVENTOR(S)      : William R. Jacobs, Jr. and Sabine Daugelat It is certified that error appears in the above-identified patent and that said Letters Patent is hereby corrected as shown below:

In Column 1, after the title, please add:

-- STATEMENT OF GOVERNMENT SUPPORT

This invention was made with government support under grant numbers AI026170 and AI033696 awarded by the National Institutes of Health. The government has certain rights in the invention. --

Signed and Sealed this
Tenth Day of November, 2015

Michelle K. Lee
*Director of the United States Patent and Trademark Office*